United States Patent [19]

Kyle

[11] Patent Number: 5,541,286
[45] Date of Patent: Jul. 30, 1996

[54] BRADYKININ ANTAGONIST PSEUDOPEPTIDE DERIVATIVES OF OLEFINIC AMINOALKANOIC ACIDS

[75] Inventor: Donald J. Kyle, Abingdon, Md.

[73] Assignee: Scios Nova Inc., Mountain View, Calif.

[21] Appl. No.: 281,907

[22] Filed: Jul. 28, 1994

Related U.S. Application Data

[63] Continuation-in-part of Ser. No. 118,981, Sep. 9, 1993, Pat. No. 5,444,048, which is a continuation-in-part of Ser. No. 957,879, Oct. 8, 1992.

[51] Int. Cl.$^6$ .................................................. A61K 38/08
[52] U.S. Cl. ........................... 530/314; 530/329; 530/330
[58] Field of Search ........................ 514/15–17; 530/328, 530/329, 314

[56] References Cited

U.S. PATENT DOCUMENTS

| 4,242,329 | 12/1980 | Claeson et al. | 424/177 |
|---|---|---|---|
| 4,483,850 | 11/1984 | Patchett et al. | 424/177 |
| 4,693,993 | 9/1987 | Stewart et al. | 514/14 |
| 4,801,613 | 1/1989 | Stewart et al. | 514/14 |
| 4,822,984 | 4/1989 | Geiger et al. | 548/252 |
| 4,923,963 | 5/1990 | Stewart et al. | 530/314 |

FOREIGN PATENT DOCUMENTS

| 0334685 | 9/1989 | European Pat. Off. . |
|---|---|---|
| 0370453 | 5/1990 | European Pat. Off. . |
| 0413277 | 2/1991 | European Pat. Off. . |
| 92/18155 | 10/1992 | WIPO . |
| 92/18156 | 10/1992 | WIPO . |
| WO94/08607 | 4/1994 | WIPO . |

OTHER PUBLICATIONS

Karanewsky et al., "(Phosphinyloxy)acyl amino acids inhibitors of angiotensin converting enzyme. 2. Terminal amino acid analogues of (S)–1–[6–amino–2[[hydroxy(4–phenylbutyl)phosphinyl]oxy]–1–oxohexyl]–L–proline" *J. Med. Chem.* (1990) 33(5):1459–1469.

Smith et al., "Synthesis and pharmacological activity of angiotensin converting enzyme inhibitors: N–(mercaptoacyl)–4–substituted–(S)–prolines" *J. Med. Chem.* (1988) 31(4):875–885.

Krapcho et al., "Angiotensin converting enzyme inhibitors. Mercaptan, carboxyalkyl dipeptide, and phosphinic acid inhibitors incorporating 4–substituted prolines" *J. Med. Chem.* (1988) 31(6):1148–1160.

Hock et al., "Hoe 140 a new potent and long acting bradykinin antagonist: in vitro studies" *Br. J. Pharmacol.* (1991) 102:769–744.

Wirth et al., "Hoe 140 a new potent and long acting bradykinin antagonist: in vivo studies" *Br. J. Pharmacol.* (1991) 102:774–777.

Pongracic et al., "A competitive kinin receptor antagonist, [DArg$^0$, Hyp$^3$, DPhe$^7$]–bradykinin, does not affect the response to nasal provocation with bradykinin" *Br. J. Pharmacol.* (1991) 31:287–294.

Higgins et al., "A study of the efficacy of the bradykinin antagonist NPC567 in rhinovirus infections in human volunteers" *Chemical Abstracts* (1991) 114:220805d.

Soler et al., "A bradykinin antagonist modifies antigen–induced airway hyper–responsiveness and airway inflammation in allergic sheep" *Am. Rev. Respir. Dis.* (1989) A327.

Stewart, John M., "Hydroxyproline analogs of bradykinin" *J. Med. Chem.* (1974) 17(5):537–539.

Stewart, John M., "Chemistry and biologic activity of peptides related to bradykinin" *Handbook of Experimental Pharmacol.* (1979) vol. XXV Supp, Springer–Verlag Berlin Heidelberg NY.

Vavrek et al., "Smooth muscle selectivity in bradykinin analogs with multiple D–amino acid substitutions", Dept. of Biochem., University of Colorado School of Medicine, Denver, Colorado.

Rifo et al., "Bradykinin receptor antagonists used to characterize the heterogeneity of bradykinin–induced responses in rat vas deferens" *Eur. J. Pharmacol.* (1987) 142:305–312.

Zeitlin et al., "Mobilization of tissue kallikrein in inflammatory disease of the colon" Wolfson Labs, Gastrointestinal Unit, West General Hospital and Dept. of Clinical Surgery, Univ. of Edinburgh (1972) pp. 113–138.

Suzuki et al., "Synthesis of every kind of peptide fragments of bradykinin" *Chem. Pharm. Bull.* (1969) 17:1671–1678.

Dray et al. "Bradykinin and inflammatory pain" *TINS* (1993) 16(3):99–104.

Perkins et al., "Antinociceptive activity of the bradykinin $B_1$ and $B_2$ receptor antagonists des–Arg$^9$, [Leu$^8$]–BK and HOE 140, in two models of persistent hyperalgesia in the rat" *Pain* (1993) 53:191–197.

Zabrocki et al., "Conformational Mimicry. 3. Synthesis and incorporation of 1,5–disubstituted tetrazole dipeptide analogues into peptides with preservation of chiral integrity: bradykinin" *J. Org. Chem.* (1992) 57(1):202–209.

Hodges et al. (eds.) *Peptides, Chemistry, Structures and Biology: Proceedings of the 13th American Peptide Symposium Jun. 20–25, 1993* (ESCOM: Leiden, 1994), pp. 381–383.

Kyle et al., "A proposed model of bradykinin bound to the rat $B_2$ receptor and its utility for drug design" *J. Med. Chem.* (1994) 37(9):1347–1354.

*Abstracts of Papers, Part 1: 208th American Chemical Society National Meeting Aug. 21–25, 1994* 190.

Kyle et al., "NMR and computational evidence that high–affinity bradykinin receptor antagonists adopt C–terminal β–turns" *J. Med. Chem.* (1993) 36(10):1450–1460.

Hodges et al. (eds.) *Peptides, Chemistry, Structure and Biology: Proceedings of the 13th American Peptide Symposium Jun. 20–25, 1993* (ESCOM: Leiden, 1994), pp. 449–451.

Primary Examiner—Howard E. Schain
Assistant Examiner—David Lukton
Attorney, Agent, or Firm—Peter R. Shearer

[57] ABSTRACT

Pseudopeptide compounds based on a modified bradykinin sequence are potent bradykinin receptor antagonists. Amino acids at at positions 2 through 5 are replaced by olefinic aminoalkenoyl groups to reduce the peptide nature of the compounds.

The analogs produced are useful in treating conditions and diseases of a mammal and human in which an excess of bradykinin or related kinins are produced or injected such as by insect bites.

2 Claims, No Drawings

BRADYKININ ANTAGONIST PSEUDOPEPTIDE DERIVATIVES OF OLEFINIC AMINOALKANOIC ACIDS

This application is a continuation-in-part of U.S. application Ser. No. 08/118,981, now U.S. Pat. No. 5,444,048, filed Sep. 9, 1993, which is a continuation-in-part of U.S. application Ser. No. 07/957,879, filed Oct. 8, 1992.

FIELD OF THE INVENTION

This invention relates to compounds which are bradykinin receptor antagonists, pharmaceutical compositions and methods for using these compounds to antagonize the effects of bradykinin in mammals, including humans. The invention relates to pseudopeptides which are potent bradykinin receptor antagonists.

More particularly, the invention relates to the replacement of the amino acids Pro-Pro-Gly-Phe found at positions 2 through 5 of bradykinin with an olefinic aminoalkenoyl. The pseudopeptide also includes additional modifications at other positions within the modified bradykinin molecule which confer increased antagonist potency, resistance to enzymatic degradation and/or tissue specificity.

BACKGROUND OF THE INVENTION

Bradykinin (BK) is a linear nonapeptide produced endogenously in humans and other mammals as a result of the activity of kallikreins, a group of proteolytic enzymes present in most tissues and body fluids, on kininogens. Once released, kinins produce many physiological responses, including pain and hyperalgesia by stimulating C- and A-fibers in the periphery. There is also considerable evidence that kinins contribute to the inflammatory response.

Native Bradykinin has the amino acid structure described on page 127 of Burch et al., (DuPont Biotech Update, 1992:4:127–140) and numerous other references.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its proinflammatory effects, bradykinin is a vasodilator. Because of its concomitant ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

As a result of the implication that increased levels of bradykinin may play a part in a number of pathological conditions, considerable research has been aimed toward the derivation of bradykinin receptor antagonists as potential therapeutic agents. A bradykinin receptor antagonist is expected to possess a number of desirable biological effects in the treatment, for example, of pain and inflammation, septic shock, airway disorders such as asthma, burn pain, pancreatitis, angioedema, certain nervous system disorders, chronic inflammation such as rheumatoid arthritis and inflammatory bowel disease, rhinitis, and allergy.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines, bradykinin-antibodies, benzodiazepine derivatives, high molecular weight ethylene oxide polymers, gallic acid esters, and serotonin inhibitors. None of these compounds or classes of compounds specifically inhibit the effects of bradykinin.

Heptyl esters of various amino acid-containing substances, such as single basic amino acids the dipeptide Phe-Gly, and analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Several research groups have prepared bradykinin receptor antagonists. The first antagonists of bradykinin were discovered by Stewart and Vavrek. U.S. Pat. Nos. 4,801,613 and 4,693,993 (which references are incorporated in their entirety herein) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY. Typically, these bradykinin antagonist peptides had $K_i$ values in the range of 20–80 nM in guinea pig ileum (Stewart, J. M., et al., In Bradykinin Antagonists (1991) Burch, R. M., Marcel Dekker, New York).

Subsequently, several classes of bradykinin antagonist peptides with 600–1000-fold greater potency in the guinea pig ileum preparation have been disclosed. Published European Patent Application No. 0 413 277 A1 to Hoechst A. G. discloses bradykinin antagonists containing the aromatic amino acid D-Phe at position 7 but containing unnatural amino acids at position 8 which impart increased potency.

Published European Patent Application No. 0 370 453 A2 to Hoechst A. G. discloses bradykinin antagonists containing a D-imino acid (D-Tic) at position 7.

A more recent series of bradykinin receptor antagonist peptides lacks the D-aromatic amino acid at position 7 which was believed to be critical to the activity of the earlier described antagonists of the endogenous neuropeptide. As described in published PCT application WO 92/18156 and WO 92/18155 (which references are incorporated in their entirety herein) this group of compounds have a general bradykinin antagonist structure wherein the L-Pro at position 7 is substituted with hydroxyproline ether and thioether derivatives (termed D-Hype) and the L-Phe at position 8 can additionally be substituted with hydroxyproline ethers and thioethers derivatives (Hype), Tic or Oic.

The bradykinin antagonist peptides referred to above exert their activity by blocking the bradykinin $B_2$ receptor. A second bradykinin receptor, the $B_1$ receptor, is not expressed to any significant degree in healthy tissue, but its expression is upregulated during persistent inflammatory hyperalgesia. This receptor is activated by des Arg[9]-kalladin and des Arg[9]-bradykinin, a proteolytic degradation product of bradykinin. It is believed to play an important role in the maintenance of hyperalgesia in chronic inflammatory conditions (Dray, A. and Perkins, M., TINS, Vol. 16, No. 3 (1993) 99–103). [Des-Arg[9]] analogs of bradykinin $B_2$ receptor antagonist peptides of the type described above bind to the $B_1$ receptor and have been shown to reverse or prevent hyperalgesia in animal models of persistent inflammatory hyperalgesia, whereas the corresponding $B_2$ receptor antagonists were ineffective or weakly active in these models (Perkins, M et al., Pain, 53, (1993) 191–197).

One limitation of the bradykinin antagonist peptides known to date is the necessity for parenteral administration. Due to the peptidic nature of the compounds, they are unlikely to be orally active. Further, peptides in general tend to have a relatively short duration of action as a consequence of their rapid matabolic degradation. As a result, non-peptide or pseudopeptide bradykinin receptor antagonists that lack the limitations of a peptide offer meaningful therapeutic advantages.

SUMMARY OF THE INVENTION

The present invention resides in the discovery that the novel pseudopeptide compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists.

More particularly, the invention relates to pseudopeptide compounds capable of binding to the bradykinin $B_2$ receptor, thereby antagonizing the effect of native bradykinin and pharmaceutically acceptable salts thereof. The bradykinin modification contemplated by this invention includes the replacement of the amino acids Pro-Pro-Gly-Phe at position 2 through 5 with an olefinic aminoalkenoyl, in addition to other modifications, to produce sequence-related analogs that act as specific and competitive inhibitors of the biological activities of bradykinin.

The invention relates more specifically to the formation of peptides having the formula:

A-B-C-D-E-F-G-Cn wherein

A is hydrogen or is selected from the group consisting of the L- and D-isomers of Arg, Gln, Asn, Lys, Sar, N-ε-acetyl-Lys, $N^G$-p-tosyl-Arg, $N^G$-nitro-Arg, Lys-Lys, acetyl-Arg, and citrulline;

B is a direct bond or is selected from the group consisting of the L- and D-isomers of Arg, Gln, Asn, Lys, Sar, N-ε-acetyl-Lys, $N^G$-p-tosyl-Arg, $N^G$-nitro-Arg, acetyl-Arg, and citrulline;

C is a $C_2$ to $C_{18}$ olefinic aminoalkenoyl having the following formula:

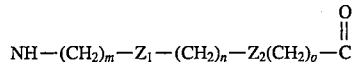

$$NH-(CH_2)_m-Z_1-(CH_2)_n-Z_2(CH_2)_o-\overset{O}{\underset{\|}{C}}$$

wherein $Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system, m, n, and o are independently 0 through 12, with the proviso that their total does not exceed 16;

D is a direct bond or is selected from the group consisting of Ser, Thr, Gly, Val, Ala, Cys and Tyr;

E is selected from the group consisting of a D-aromatic amino acid and a D-Hype;

F is selected from the group consisting of Oic, Aoc, Thz, Tic, L-indoline-2-carboxylic acid, Aib, Leu, Ile, Val, Thi, octahydro-1H-isoindole-1-carboxylic acid, pipecolinic acid, Pro, 4Hyp, azetidine-2-carboxylic acid, Phe, homoPhe, and a Hype;

G is selected from the group consisting of Arg, Orn, Asn, Gln, and Lys;

Cn is a hydroxyl group or a C-terminal extension selected from the group consisting of amide, alkoxy, and an acidic, basic, or neutral aliphatic, aromatic, or cyclic amino acid residue of the D- or L-configuration; and pharmaceutically accepted salts thereof.

In another embodiment, the invention relates to pseudopeptide compounds capable of binding to the bradykinin $B_1$ receptor. These compounds, because of their ability to block $B_1$ receptor mediated hyperalgesia, are useful in the treatment of conditions associated with chronic inflammation. In particular, these compounds have the same structure as that set forth above for the $B_2$ receptor antagonists with the exception that the group represented by G is deleted.

Another embodiment of the invention involves a pharmaceutical composition useful as a bradykinin receptor antagonist comprising a pharmaceutical carrier and an effective amount of the novel bradykinin-type pseudopeptide. The invention also involves a process for antagonizing bradykinin receptor activity in mammals which comprises administering to a subject an effective amount of the novel compound to antagonize bradykinin receptor activity.

A further embodiment involves a pharmaceutical preparation for treating local pain and inflammation from burns, wounds, cuts, rashes and other such trauma, and pathological conditions caused by the production of bradykinin or related kinins by an animal which comprises administering an effective amount of the novel pseudopeptide sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

The pseudopeptide compounds of the present invention are bradykinin receptor antagonists wherein an organic group exemplified by an olefinic aminoalkenoyl group substitutes and mimics the function of amino acids 2 through 5 (Pro-Pro-Gly-Phe) of native bradykinin. Any bradykinin-type molecule containing an olefinic aminoalkenoyl substituent at positions 2 through 5 is contemplated by this invention.

A. Preferred Bradykinin-Type Peptide Structures

The preferred bradykinin-type peptides have the following formula:

FORMULA 1

A-B-C-D-E-F-G-Cn wherein

A is hydrogen or is selected from the group consisting of the L- and D-isomers of
Arg, Gln, Asn, Lys, Sar, N-ε-acetyl-Lys, $N^G$-p-tosyl-Arg, $N^G$-nitro-Arg, Lys-Lys, acetyl-Arg, and citrulline;

B is a direct bond or is selected from the group consisting of the L- and D-isomers of Arg, Gln, Asn, Lys, Sar, N-ε-acetyl-Lys, $N^G$-p-tosyl-Arg, $N^G$-nitro-Arg, acetyl-Arg, and citrulline;

C is a $C_2$ to $C_{18}$ olefinic aminoalkenoyl having the following formula:

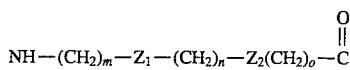

wherein $Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system, m, n, and o are independently 0 through 12, with the proviso that their total does not exceed 16;

D is a direct bond or is selected from the group consisting of Ser, Thr, Gly, Val, Ala, Cys and Tyr;

E is selected from the group consisting of a D-aromatic amino acid and a D-Hype;

F is selected from the group consisting of Oic, Aoc, Thz, Tic, L-indoline-2-carboxylic acid, Aib, Leu, Ile, Val, Thi, octahydro-1H-isoindole-1-carboxylic acid, pipecolinic acid, Pro, 4Hyp, azetidine-2-carboxylic acid, Phe, homoPhe, and a Hype;

G is selected from the group consisting of Arg, Orn, Asn, Gln, and Lys;

Cn is a hydroxyl group or a C-terminal extension selected from the group consisting of amide, alkoxy, and an acidic, basic, or neutral aliphatic, aromatic, or cyclic amino acid residue of the D- or L-configuration; and pharmaceutically accepted salts thereof.

FORMULA 2

Particularly preferred is a peptide wherein:

A is D-Arg;

B is Arg;

C is a $C_2$ to $C_{18}$ olefinic aminoalkenoyl having the following formula:

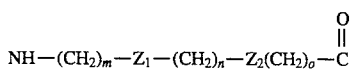

wherein $Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system, m, n, and o are independently 0 through 12, with the proviso that their total does not exceed 16;

D is a direct bond or selected from the group consisting of Ser, Gly and Val;

E is selected from the group consisting of D-Phe, D-Tic and a D-Hype;

F is selected from the group consisting of Phe, Oic, Aoc, and a Hype;

G is Arg; and $C_n$ is selected from the group consisting of a hydroxyl group, an amide group and an alkoxy group.

FORMULA 3

If one wishes to produce a bradykinin antagonist which interacts with the $B_1$ receptor and is therefore useful for the treatment of chronic inflammatory conditions, then the pseudopeptide has the preferred formula A-B-C-D-E-F-Cn wherein A, B, C, D, E, and F are as described above for Formula 1.

Particularly preferred $B_1$ receptor antagonists of this formula are those which A, B, C, D, E and F are described above for Formula 2.

B. Preferred Olefinic Aminoalkenoyl Structures

C is a $C_2$ to $C_{18}$ olefinic aminoalkenoyl having the following formula:

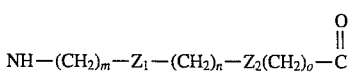

wherein $Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system, hydroxymethyl, $C_1$ to $C_6$ alkyl and benzyl, m, n, and o are independently 0 through 12, with the proviso that their total does not exceed 16;

An olefinic aminoalkenoyl is a carbon chain of from 2 to 18 carbons containing at least one double bond having an amino acid linkage (i.e., an N-terminal amino group and a C-terminal carbonyl group). An olefinic aminoalkenoyl may contain multiple double bonds. Two to four of the carbons in the alkenyl portion of the olefinic aminoalkenoyl may be optionally incorporated into a ring structure. The ring structure may or may not contain double bonds (e.g., cycloalkenyl or cycloalkyl). The alkenyl portion of the olefinic aminoalkenoyl is preferably a hydrocarbon chain, but may also include carbon replacements, such as by nitrogen.

Preferably the olefinic aminoalkenoyls of C include those wherein $Z_1$ is selected from the group consisting of a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

$Z_2$ is selected from the group consisting of a direct bond, and a $C_2$ to $C_{18}$ monoolefin;

m, n, and o are independently 0 to 6.

Preferred cyclic systems incorporated into the $Z_1$ polyolefins include but are not limited to,

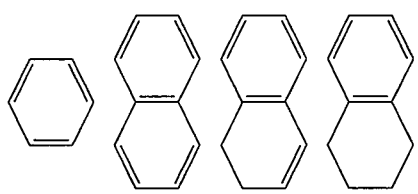

Other preferred peptides include those wherein the olefinic aminoalkenoyl of C is selected from the group consisting of:

4-amino-2-butenoyl;

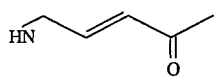

3-[2-(aminomethyl)phenyl]-2-propenoyl;

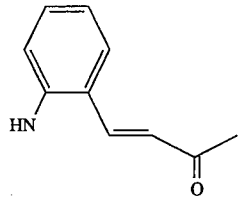

3-[ 2-(aminomethyl)phenyl]-2-propanoyl;

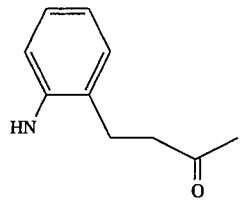

3-[3-(aminomethyl)phenyl]-2-propenoyl;

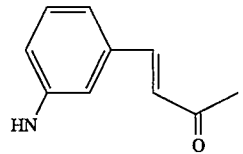

3-[3-(aminomethyl)phenyl]-2-propanoyl;

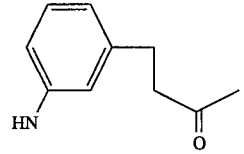

4-[2-(aminomethyl)phenyl]-3-butenoyl;

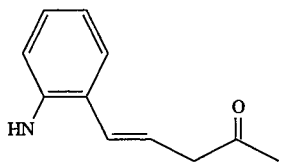

3-[2-(aminoethyl)phenyl]-2-propenoyl;

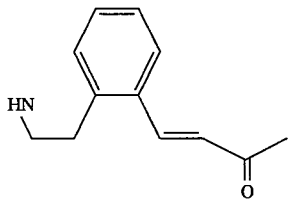

6-amino-4,5-(1,2-cyclohexyl)-2-hexenoyl.

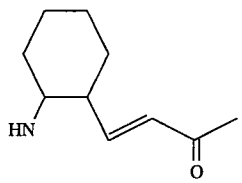

Additional olefinic aminoalkenoyls suitable for use as substituent include:

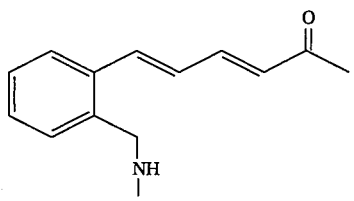

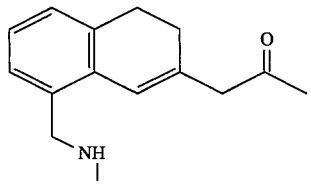

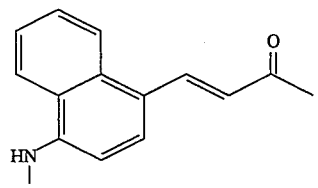

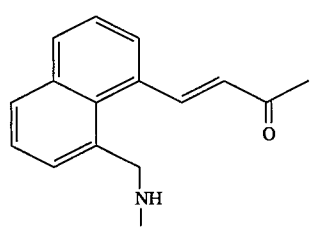

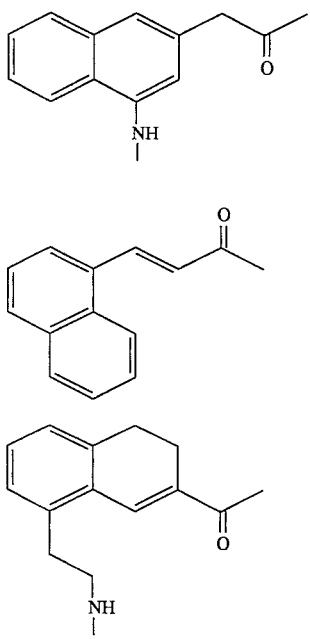
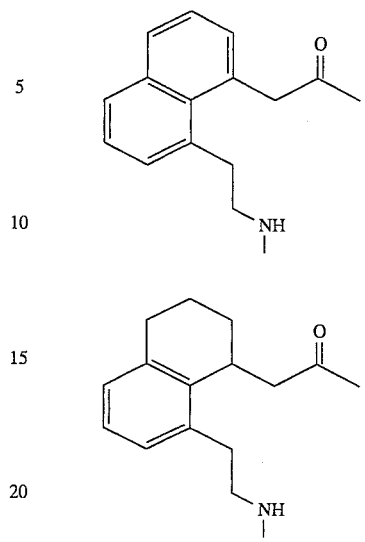
C. Specifically Preferred Peptides
Particularly preferred are the following peptides:
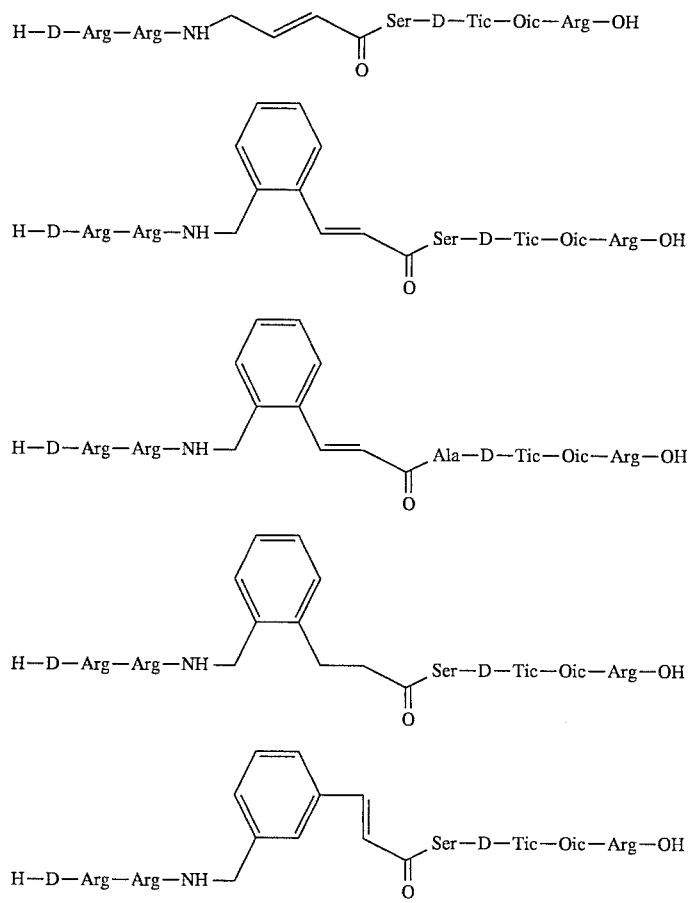

-continued
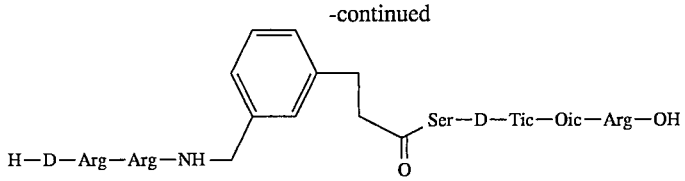
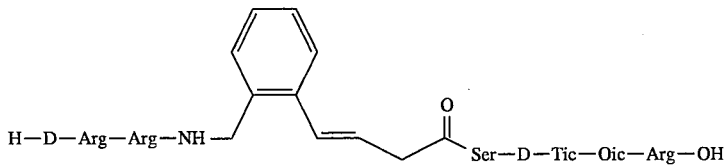
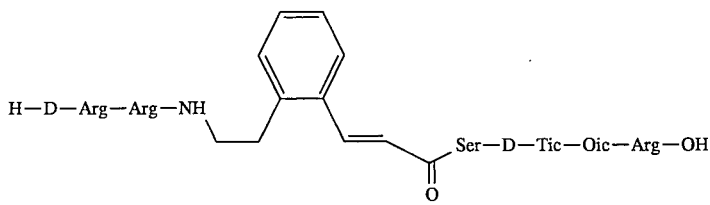
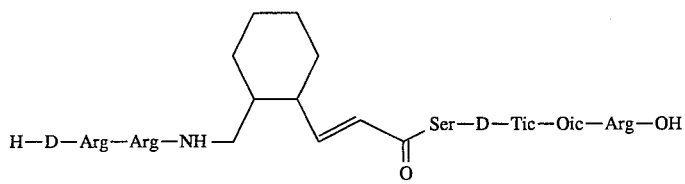
Particularly preferred $B_1$ receptor antagonists, for the treatment of chronic inflammatory conditions, are those in which the C-terminal arginine group in the preceding formulae is deleted, i.e. Oic is the C-terminal residue.
Other pseudopeptides of the invention include:
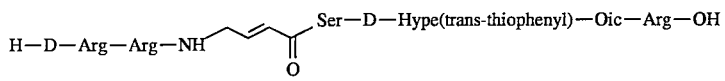
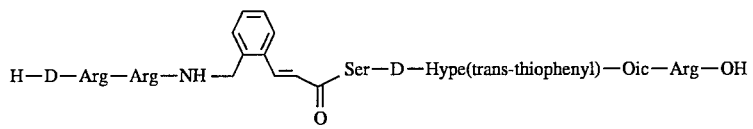
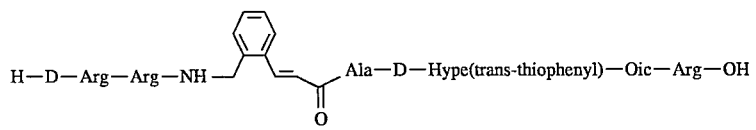
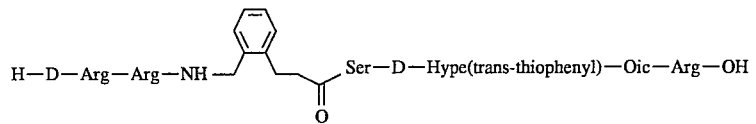
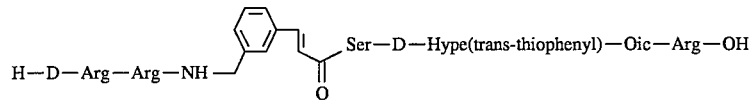
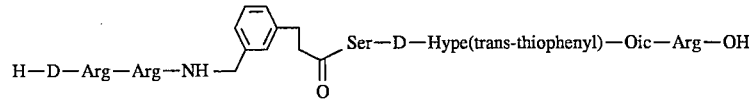

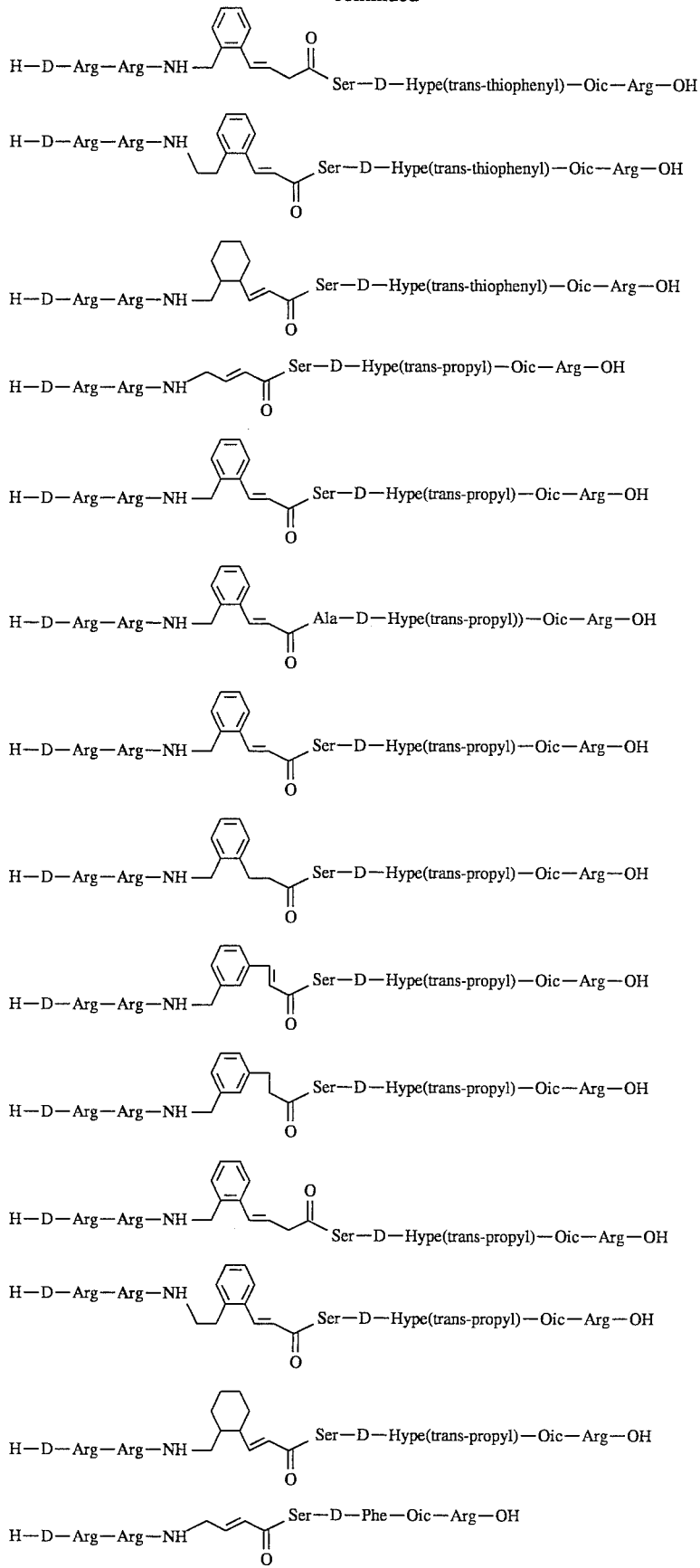

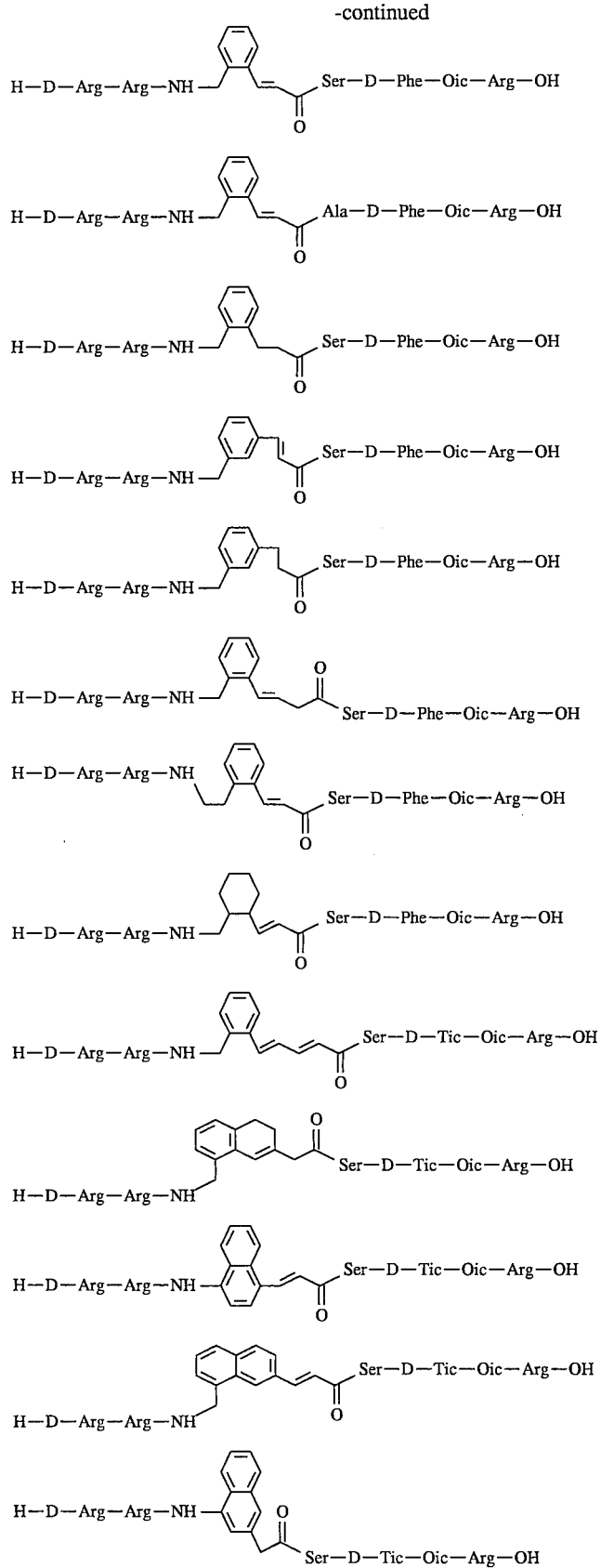

-continued

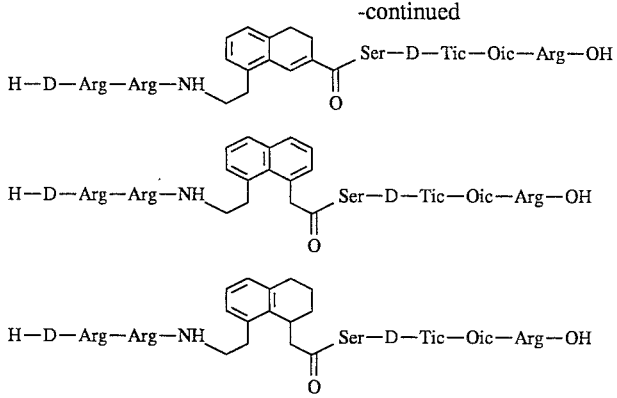

Other useful $B_1$ receptor antagonists for the treatment of chronic inflammation are those of the preceding formulae in which the C-terminal arginine residue is deleted, i.e. Oic is the C-terminal residue.

The following terms used herein in the specification and claims are further defined: "olefinic aminoalkenoyl" is a carbon chain of from 2 to 18 carbons containing at least one double bond, wherein 2 to 4 carbons may be optionally incorporated into a cyclic structure, having an amino acid linkage (i.e., an N-terminal amino group and a C-terminal carbonyl group). The alkenyl portion of the olefinic aminoalkenoyl is preferably a hydrocarbon chain, but may also include carbon replacements, such as by nitrogen.

"Hype" is defined herein as having the following structure:

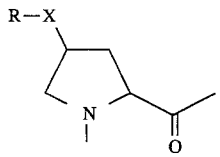

wherein

R is selected from the group consisting of H, $C_1$–$C_6$ alkyl, substituted $C_1$–$C_6$ alkyl, $C_2$–$C_8$ alkenyl, $C_2$–$C_8$ cycloalkyl, $C_3$–$C_8$ cycloalkyl substituted $C_1$–$C_6$ alkyl, an aryl group, a substituted aryl group wherein the substituent is $C_1$–$C_4$ alkyl, $C_1$–$C_4$ alkoxy, halogen or trifluoromethyl, an arylalkyl group, and a group of the formula $R^1$NHC(O) where $R^1$ is $C_1$–$C_6$ alkyl or aryl, and where X is either $SO_n$ or oxygen, and n=0, 1, or 2;

"carbocycle" and "cycloalkyl" are interchangeably defined herein as a saturated cyclic hydrocarbon structure, such as cyclohexyl, cyclopropyl, cyclobutyl, cyclopentyl and cycloheptyl;

"olefin" and "cycloalkenyl" are defined herein as a cyclic hydrocarbon structure containing at least one double bond and includes substituted aryl groups, such as 1,2-, 1-3 and 1,4-phenylene, benzyl, phenyl, cyclohexenyl, cyclohexadienyl, cyclopentadienyl. Also included in this definition are multiple ring structures, such as naphthyl;

"pseudopeptide" is an entity which is partially amino acid (peptidic) in nature and partially organic chemical in nature. A minimum of two peptide bonds are eliminated and replaced by organic molecules having the ability to retain the functionality of amino acids they replace in the pseudopeptides of the present invention;

"alkenyl" and "olefin" are interchangeably defined herein as a hydrocarbon structure containing at least one double bond, suitable alkenyls can also be hydrocarbon structure containing multiple double bonds, the double bonds can optionally be incorporated into a ring structure, such as a cycloalkenyl;

"amino acid linkage" is exemplified by a moiety having a N-terminal amino group and a C-terminal carbonyl group;

"alkyl" is a paraffinic hydrocarbon group which may be derived from an alkane by dropping one hydrogen from the formula, such as methyl, ethyl, propyl, isopropyl, butyl, and so forth;

"substituted $C_1$–$C_6$ alkyl" is a branched alkyl, such as methylbutyl;

"aryl" is an aromatic ring compound such as phenyl, naphthyl;

"substituted aryl" is a substituted aromatic ring including, but not limited to, nitro substitution, or halogen substitution; and "aralkyl" is a aryl being attached through an alkyl chain, straight or branched, containing from one through six carbons, such as a phenylpropyl group.

A "direct bond" is a bond which replaces a particular amino acid compound between adjacent amino acids and which amino acid may also be indicated to be absent by the term "null".

The phrase "a suitable amine protecting group" is a group, such as Boc (t-butyloxycarbonyl-) which protects the amine moiety from reaction and which can be removed under mild conditions so as not to affect the rest of the molecule.

Definitions of the amino acid abbreviations used herein are as follows:

"aromatic amino acid" is a naturally occurring or non-naturally occurring amino acid having one or more unsaturated carbon rings and includes, but is not limited to, Phe, Tic, Thi, n-benzyl Gly, homoPhe, Tyr, Trp, Nal.

Arg is arginine; Ala is alanine; Aib is 2-aminoisobytyric acid; Aoc is (S,S,S)-2-azabicyclo[3.3.0]octane-3-carboxylic acid; Asn is asparagine; Asp is aspartic acid;

Cys is cysteine; Eac is ε-aminocaproic acid; Gln is glutamine; Glu is glutamic acid; Gly is glycine; Ile is isoleucine; Leu is leucine; Lys is lysine; Met is methionine; Nal is beta-2-naphthylalanine; Orn is ornithine; Pro is proline; dehydroPro is 3,4-dehydroproline, homoPhe is homophenylalanine; 4Hyp is 4-hydroxyproline; Ser is serine; Sar is sarcosine; Thi is beta-2-thienylalanine; Thr is threonine; Thz is thiazolidine-4- carboxylic acid; Phe is phenylalanine; phenylGly is 2-phenylglycine; Tic is tetrahydroisoquinoline-3-carboxylic acid; Oic is (2S, 3aS, 7aS)-octahydro-1H-indole-2-carboxylic acid; Val is valine; prenyl is a 3-methyl-2-butenyl 4S-D-prolyl propyl ether and represents radical. D-Hype (trans-propyl) is

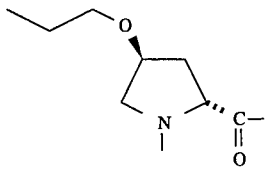

D-Hype (trans-thiophenyl) is 4S- D-prolyl phenyl thioether, also known as D-4-hydroxyproline trans phenylthioether also known as D-Hyp S(trans-phenyl) and represents

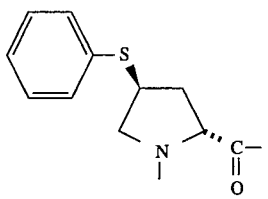

D-Hype(trans-phenylpropyl) represents

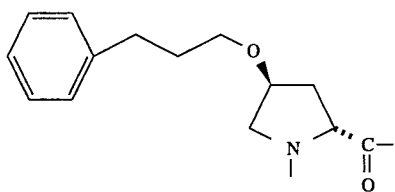

D-Hype(trans-2-methylbutyl) represents

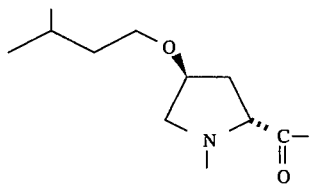

D-Hype(trans-ethyl) represents

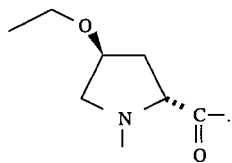

D-Hype(trans-methyl) represents

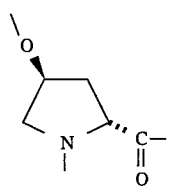

Aoc can be prepared by the method of V. Teetz, R. Geiger and H. Gaul, *Tetrahedron Lett,* (1984), 4479. Tic is commercially available from Bachem Biosciences or can be prepared by the method of K. Hayashi, Y. Ozaki, K. Nunami and N. Yoneda, *Chem. Pharm, Bull,* (1983) 31, 312.

All amino acids residues, except Gly and Ser, described in the specification are preferably of the L-configuration unless otherwise specified. It would be recognized, however, that the 7 position amino acids and derivatives must always be the D-configuration whereas the amino acids and derivatives of position 8 may be either in the D- or L- configuration. The hydroxyproline ethers at position 7 are preferably in a trans configuration, whereas the hydroxyproline ethers at position 8 can be in either the cis or trans configuration. The symbols and abbreviations used for amino acids, their derivatives and protecting groups, and peptides and their salts are those customarily used in peptide chemistry. (See *Biochem. J.* (1972), 126, 773), which Journal reference is hereby incorporated by reference.

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie,* (1974), Vol. 16, parts I & II for solution-phase synthesis, and in *Solid Phase Peptide Synthesis,* (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate hydroxyproline substituents used at position 7 or 8 are prepared by the process described in PCT publications WO 92/18155 and WO 92/18156 which are herein incorporated by reference. The starting materials are commercially available and can be prepared by known procedures. Both the cis and trans stereoisomers can be prepared by these means and are within the scope of the present invention.

The olefinic aminoalkenoyl substituents used to replace the amino acids at positions 2 through 5 are prepared using various conventional chemical synthetic procedures that are well known to those skilled in the art. Various general prototypic sequences are outlined in Schemes I through VI.

The preparation of compounds for administration in pharmaceutical preparations may be performed in a variety of methods well known to those skilled in the art. Appropriate pharmaceutically acceptable salts within the scope of he invention are those derived from mineral acids such as hydrochloric acid, hydrobromic acid, phosphoric acid, nitric acid, and sulfuric acid; and organic acids such as tartaric acid, fumaric acid, lactic acid, oxalic acid, ethylsulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively.

The compounds of the invention contain asymmetric centers. Thus, the invention includes the individual stereoisomers, and the mixtures thereof. The individual isomers may be prepared or isolated by methods known in the art.

ADMINISTRATION AND USE

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include inflammatory disorders such as shock, systemic inflammatory response syndrome, pancreatitits, and angioedema, arthritis and inflammatory bowel disease, systemic treatment of pain and inflammation, local trauma such as wounds, burns, rashes, airway disorders such as asthma, rhinitis and allergies, and nervous system diseases such as spinal cord injury, stroke, hemorrhage, trauma, tumors, abcess and encephalitis. The compounds of the invention which are $B_1$ receptor antagonists are useful, alone or in combination with the $B_2$ receptor antagonists, for the treatment of conditions associated with persistent inflammatory hyperalgesia, e.g. rheumatoid arthritis.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral adminstration may be coated or other pharmaceutically acceptable agents and formulation may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs are suitably prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 500 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, intraveneously, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel compounds are potent, selective bradykinin receptor antagonists.

The following examples are illustrative of preferred embodiments of methods of preparation and compounds of the invention and are not to be construed as limiting the invention thereto.

EXAMPLES

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie*, (1974), Vol. 16, parts I & II for solution-phase synthesis, and in *Solid Phase Peptide Synthesis*, (1984), by Stewart and Young for synthesis by the solid phase method of Merrifield.

The olefinic aminoalkenoyl substituents used to replace the amino acids at positions 2 through 5 are prepared using various conventional chemical synthesis procedures that are well known to those skilled in the art. Various general sequences are outlined in Schemes I through VI.

Any chemist skilled in the art of peptide synthesis can synthesize the peptides of this invention by standard solution methods or by manual or automated solid phase methods.

SCHEME I

N-Boc-protected 3-[2-(aminomethyl)phenyl]-2-propenoic acid (Compound 1) and N-Boc-protected 3-[2(aminomethyl)phenyl]-2-propanoic acid (Compound 2) were prepared via the following scheme.

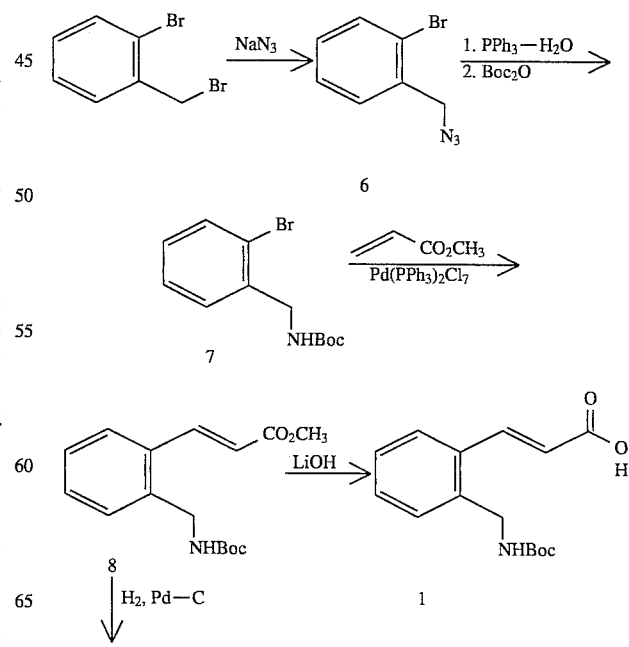

SCHEME III

N-Boc-protected 4-[2-(aminomethyl)phenyl]-3-butenoic acid (Compound 5) was prepared via the following scheme.

SCHEME II

N-Boc-protected 3-[3-(aminomethyl)phenyl]-2-propenoic acid (Compound 3) and 3-[3-(aminomethyl)phenyl]-2-propanoic acid (Compound 4) were prepared by the following scheme.

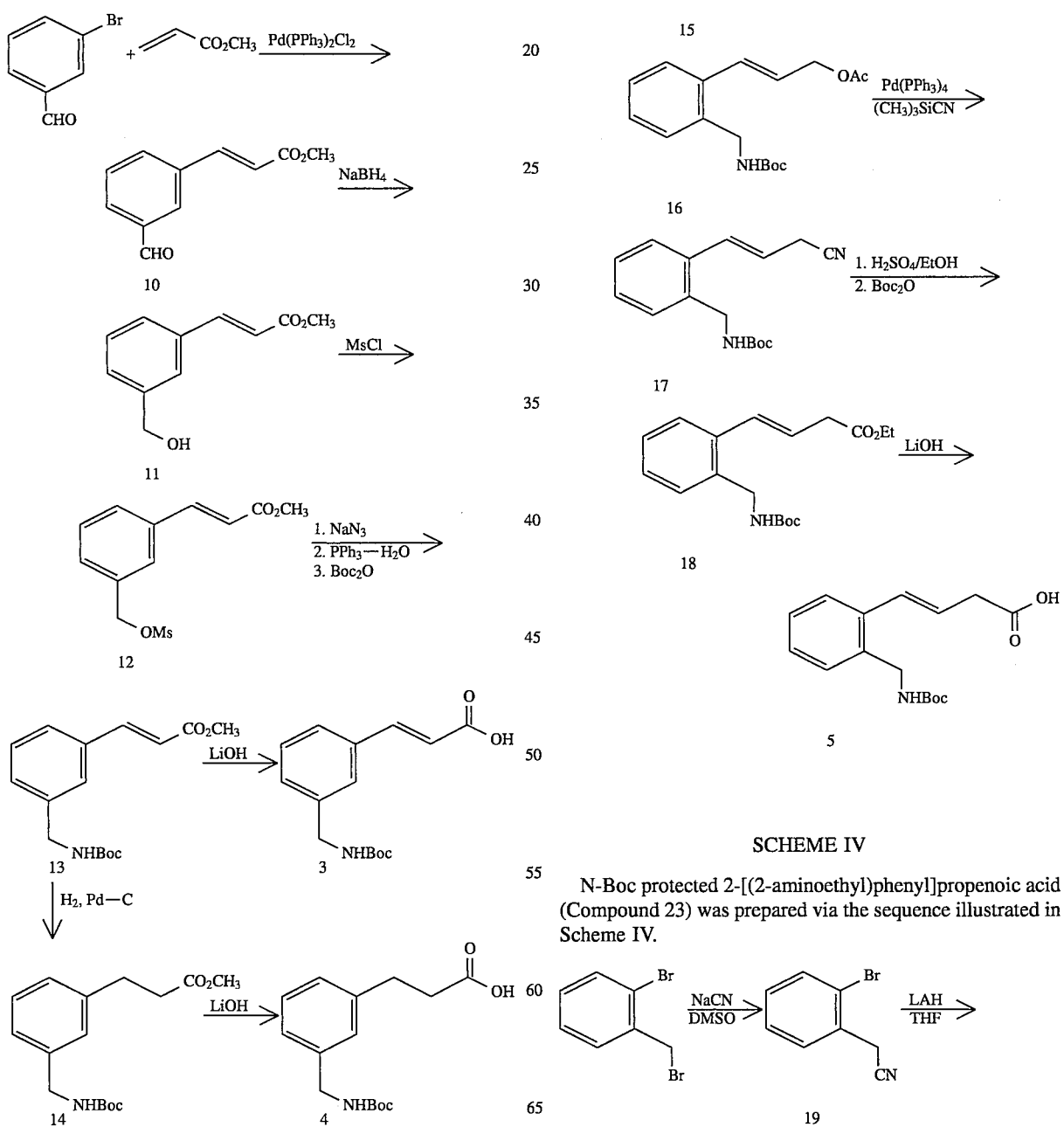

SCHEME IV

N-Boc protected 2-[(2-aminoethyl)phenyl]propenoic acid (Compound 23) was prepared via the sequence illustrated in Scheme IV.

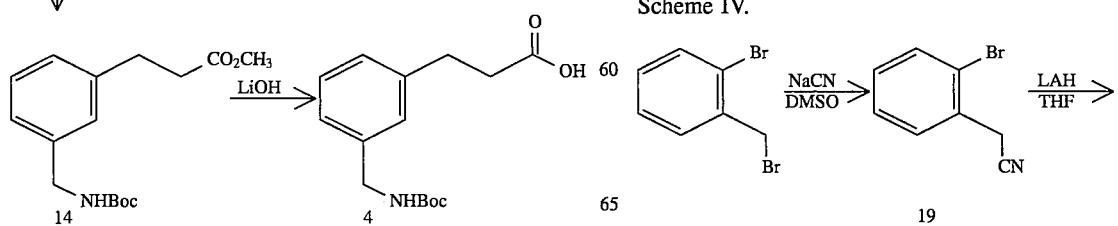

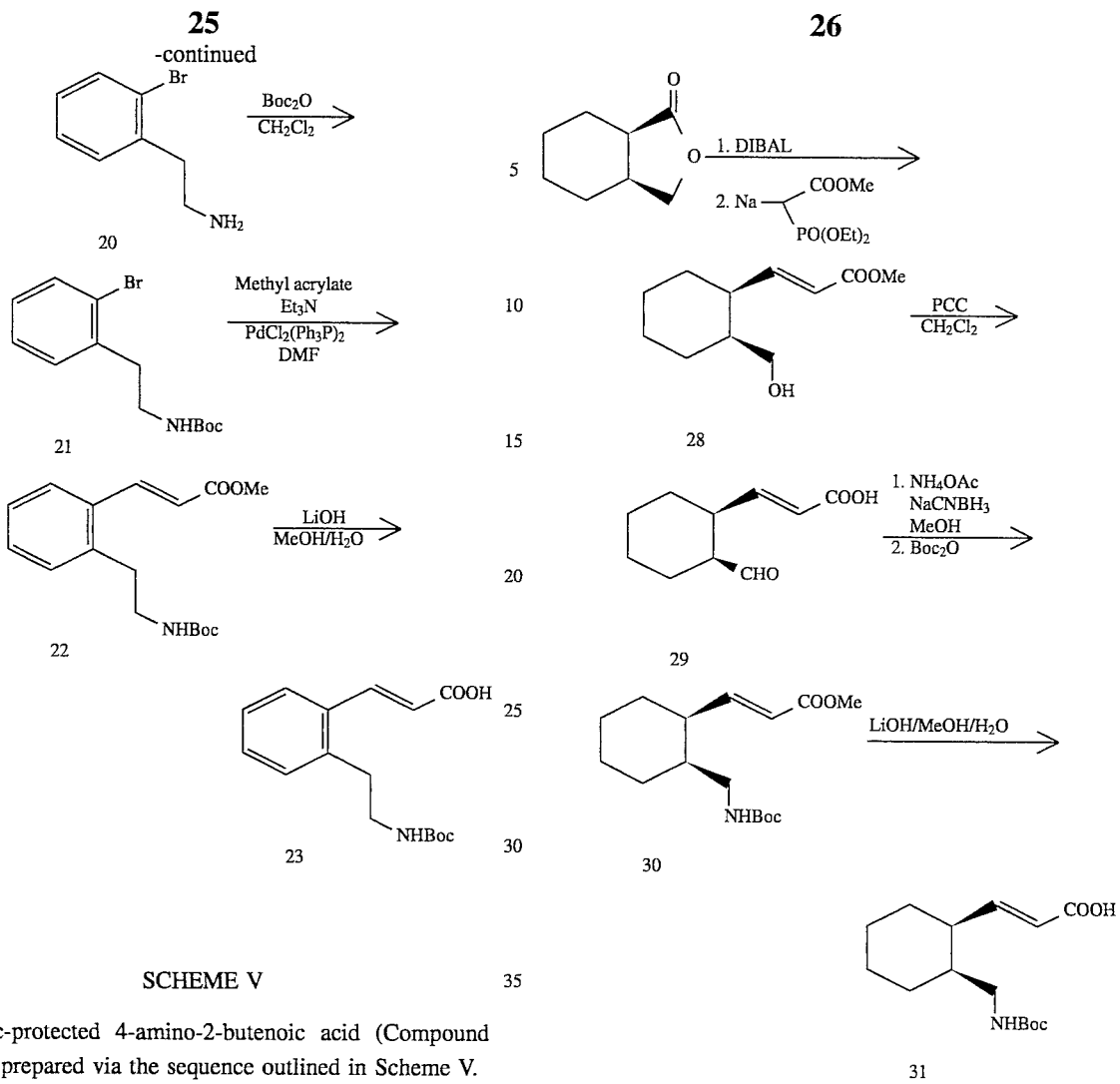

SCHEME V

N-Boc-protected 4-amino-2-butenoic acid (Compound 27) was prepared via the sequence outlined in Scheme V.

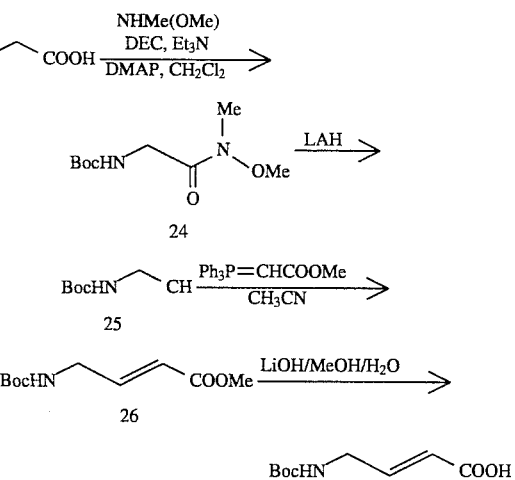

SCHEME VI

N-Boc-protected 6 amino-4,5-(1,2-cyclohexyl)-2-hexanoic acid (Compound 31) and its isomer (Compound 32) were prepared via the sequence outlined in Scheme VI.

EXAMPLE 1

Preparation of N-Boc-protected 3-[2-(aminomethyl)phenyl]-2-propenoic acid

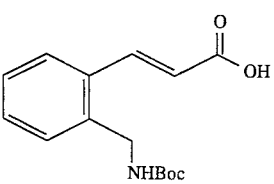

N-Boc-protected 3-[2-(aminomethyl)phenyl]-2-propenic acid (Compound 1) was prepared as described previously in Scheme I. A mixture of 15.0 g (60.0 mmol) of 2-bromobenzyl bromide and 11.7 mg (180 mmol) of NaN₃ in 100 ml of DMF was stirred at room temperature for 26 hours. The mixture was poured into 200 ml of H₂O, extracted with ethyl acetate (3×250 ml). The extract was washed with water (3×300 ml ), dried over MgSO₄, and concentrated to give 12.5 g of crude product 6 .

To a solution of azide 6 (1.4 g, 6.6 mmol) in 20 ml of THF containing 5 ml of H₂O was added in small portions triphenyl phosphine (2.3 g, 9.0 mmol) at room temperature. The mixture was stirred for 24 hours. Di-tert-butyl dicarbonate (2.2 g, 10 mmol) was added. The mixture was heated at 70° C. for 1 hour, cooled to room temperature and concentrated. The residue was redissolved in EtOAc (100 ml), washed with brine, dried over MgSO₄ and concentrated. Silica gel chromatography with 5% EtOAc-hexane gave 2.0 g of compound 7 as a colorless oil.

A mixture of bromide 7 (2.0 g, 6.99 mmol), methyl acrylate (0.722 g, 8.39 mmol), palladium (II) bis triphenyl phosphine dichloride (98 mg, 0.14 mmol), triethylamine (3 ml, 21.5 mmol) in DMF (10 ml) was heated under argon at 90° C. for 24 hours. The reaction mixture was then cooled to room temperature, poured into 100 ml of H₂O, extracted with ethyl acetate (100 ml×3). The organic layer was dried over MgSO₄ and concentrated. Silica gel chromatography of the residue gave 1.67 g compound 8 as pale yellow solid.

To a solution of the ester 8 (1.50 g, 5.15 mmol) in THF (15 ml) was added dropwise to give 1.0 g N-Boc-protected 3-[2-(aminomethyl)phenyl]-2propenoic acid (compound 1) as white solid.

EXAMPLE 2

Preparation of N-Boc-protected 3-[2-(aminomethyl)phenyl]-2-propanoic acid

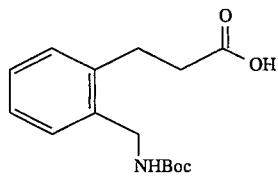

N-Boc-protected 3-[2-(aminomethyl)phenyl]-2-propanoic acid (Compound 2) was prepared as outlined in Scheme I. Compound 8 was prepared as described in Example 1. Compound 9 was prepared from Compound 8, by high pressure hydrogenation (40 psi) in CH₃OH with palladium on carbon as catalyst. N-Boc-protected 3-[2-(aminomethyl)phenyl]-2-propanoic acid (compound 2) (white solid, 1.4 g) was prepared from compound 9 (2.0 g) in THF by dropwise adding LiOH solution (1M, 6.2 ml, 6.2 mmol) at 0° C. The mixture was stirred at 0° C. for 15 minutes then at room temperature overnight. After removal of most of THF under reduced pressure, the mixture was diluted with H₂O (50 ml) and extracted ether (20 ml). The aqueous solution was acidified with 10% citric acid. The resulting white solid was collected by filtration, washed with 2 ml of cold water and dried under vacuum.

EXAMPLE 3

Preparation of N-Boc-protected 3-[3-(aminomethyl)phenyl]-2-propenoic acid

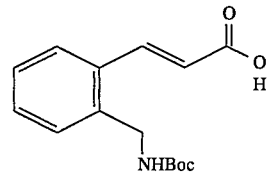

N-Boc-protected 3-[3-(aminomethyl)phenyl]-2-propenoic acid (Compound 3) was prepared as outlined in Scheme II. A mixture of 3-bromobenzaldehyde (2.0 g, 10.8 mmol), methyl acrylate (1.1 g, 12.8 mmol), palladium (II) bis triphenyl phosphine dichloride (98 mg, 0.14 mmol) and triethylamine (3 ml, 21.5 mmol) in DMF (10 ml) was heated under argon at 90° C. for 24 hours. The reaction mixture was then cooled to room temperature, poured into 100 ml of H₂O, extracted with ethyl acetate (3×100 ml). The organic layer was dried over MgSO₄ and concentrated. Silica gel chromatography of the residue gave 2.0 g compound 10 as a pale yellow oil.

To a solution of the aldehyde 10 (5.0 g, 15.8 mmol) in methanol (40 ml) cooled to 0° C. was added in small portions NaBH₄ (358 mg, 9.46 mmol). The mixture was stirred at 0° C. for 30 minutes. Water (10 ml) was added dropwise and the mixture was stirred at 0° C. for an additional 30 minutes. Methanol was removed. The aqueous layer was diluted with water (10 ml) and extracted with ethyl acetate (3×20 ml). The organic layer was washed with brine (20 ml), dried over MgSO₄ and concentrated. Silica gel chromatography of the residue with 25% ethyl acetate-hexane gave 3.4 g of compound 11.

To a solution of the alcohol 11 (3.3 g, 17.2 mmol), triethylamine (3.6 ml, 25.8 mmol) in methylene chloride (40 ml) cooled to −10° C. was added dropwise methylsulfonyl chloride (1.46 ml, 18.9 mmol). The mixture was stirred at −10° C. for 30 minutes, diluted with methylene chloride (40 ml), washed with water (2×50 ml), dried over MgSO₄ and concentrated to give compound 12 (4.3 g). The crude material thus obtained was used in next reaction without purification.

A mixture of mesylate 12 (4.3 g, 15.9 mmol) and sodium azide (2.1 g, 31.85 mmol) in DMF (30 ml) was stirred at room temperature for 4 hours. The mixture was diluted with ether (200 ml). The white solid was removed by filtration. The ether in the titrate was removed under reduced pressure. To the residue was added THF (40 ml) and water (20 ml). Triphenyl phosphine (6.4 g, 23.8 mmol) was added in small portions next. The mixture was stirred at room temperature overnight.

To the above mixture was added di-tert-butyl dicarbonate (5.9 g, 27.1 mmol). The mixture was heated at 70° C. for 1 hour, cooled to room temperature, and poured into 200 ml of ice-water mixture. The mixture was extracted with ethyl acetate (3×100 ml), dried and concentrated. Silica gel chromatography of the residue gave compound 13 (3.93 g, 78% from alcohol 11) as colorless oil.

N-Boc-protected 2-[3-(aminomethyl)phenyl]-2-propenoic acid (compound 3)(1.38 g, white solid) was prepared from ester 13 (1.77 g) in THF by dropwise adding LiOH solution (1M, 6.2 ml, 6.2 mmol) at 0° C. The mixture was stirred at 0° C. for 15 minutes then at room temperature overnight. After removal of most of THF under reduced pressure, the mixture was diluted with H₂O (50 ml) and extracted with ether (20 ml). The aqueous solution was acidified with 10% citric acid. The resulting white solid was collected by filtration, washed with 2 ml of cold water and dried under vacuum.

EXAMPLE 4

Preparation of N-Boc-protected 3-[3-(aminomethyl)phenyl]-2-propanoic acid

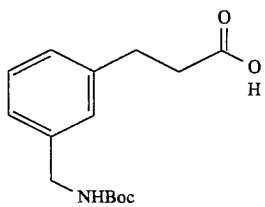
4

N-Boc-protected 3-[3-(aminomethyl)phenyl]-2-propanoic acid (Compound 4) was prepared as outlined in Scheme II. A mixture of compound 13 (1.16 g) prepared as described in Example 3, 10% Pd-C (100 mg), and methanol (80 ml) was shaken under hydrogen (40 psi) on a Parr shaker for 6 hours. The mixture was filtered and the filtrate concentrated to give the saturated ester 14 (1.2 g) as colorless oil.

N-Boc-protected 3-[3-(aminomethyl)phenyl]-2-propanoic acid (compound 4) (0.84 g, white solid) was prepared from ester 14 (1.2 g) in THF by dropwise adding LiOH solution (1M, 6.2 ml, 6.2 mmol) at 0° C. The mixture was stirred at 0° C. for 15 minutes then at room temperature overnight. After removal of most of THF under reduced pressure, the mixture was diluted with H₂O (50 ml) and extracted with ether (20 ml). The aqueous solution was acidified with 10% citric acid. The resulting white solid was collected by filtration, washed with 2 ml of cold water and dried under vacuum.

EXAMPLE 5

Preparation of N-Boc-protected 4-[2-(aminomethyl)phenyl]-3-butenoic acid

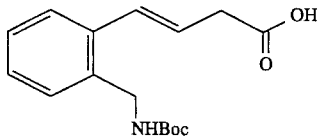
5

N-Boc-protected 4-[2-(aminomethyl)phenyl]-3-butenoic acid (Compound 5) was prepared as outlined in Scheme III. Under argon, a solution of DIBAL-H in hexane (1.5M, 21 ml, 31.8 mmol) was added dropwise to a solution of compound 8 as prepared in Example 1 (4.0 g) in THF (80 ml) cooled at −78° C. The mixture was stirred at −78° C. for 30 minutes and then at room temperature for 2 hours. The reaction was quenched with 50 ml of saturated potassium sodium solution at 0° C. The mixture was stirred at room temperature for 2 hours and extracted ethyl acetate (3×100 ml). The organic layer was washed with brine (2×200 ml), dried over Na₂SO₄ and concentrated to give 4.0 g crude alcohol 15.

To a solution of the alcohol 15 (4.0 g, 14.6 mmol) and pyridine (2.5 ml, 30.9 mmol) in CH₂Cl₂ (50 ml) cooled to 0° C. was added acetyl chloride (1.5 ml, 21.1 mmol) dropwise. After the mixture was stirred at 0° C. for 2 hours, it was diluted with CH₂Cl₂ (100 ml), washed sequentially with water (50 ml), 1N HCl (50 ml) and brine (50 ml). The organic layer was dried over Na₂SO₄, concentrated to give 3.65 g of the crude acetate 16.

A mixture of the acetate 16 (3.0 g, 9.6 mmol), TMSCN (2.6 ml, 27.1 mmol), Pd(PPh₃)₄ (1.1 g, 0.95 mmol) in THF (25 ml) was refluxed under argon for 36 hours. The mixture was concentrated. Silica gel chromatography of the residue gave 0.5 g desired compound 17 as a pale yellow oil.

A solution of the nitrile 17 (0.27 g) in ethanol (1 ml) was added to a solution of concentrated the H₂SO₄ (0.5 ml) in ethanol (2 ml). The mixture was heated for 20 hours at 120° C. in a pressure tube charged with argon. The mixture was cooled to room temperature and poured into 20 ml of ice-water. The mixture was extracted with ether (10 ml). The aqueous layer basified to pH 8 by Na₂CO₃ and the mixture was extracted with ethyl acetate (3×20 ml). The organic layer was washed with brine (20 ml), dried (Na₂SO₄) and concentrated.

The residue was dissolved in dioxane (5 ml). To the solution was added di-tert-butyl dicarbonate (0.3 g). The mixture was heated at 80° C. for 90 minutes, cooled and concentrated. The residue was purified by silica gel chromatography to give 0.3 g compound 18.

Ester 18 (0.3 g) was hydrolyzed with LiOH by the same procedure utilized to prepare compound 1 as described in Example 1 to give N-Boc-protected 4-[2-(aminomethyl)phenyl]-3-butenoic acid (compound 5)(210 mg) as white solid foam.

EXAMPLE 6

Synthesis of N-Boc-protected 3-[2-(aminoethyl)phenyl]-2-propenoic acid

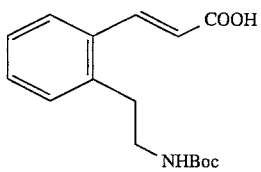
23

N-Boc-protected 3-[2-(aminoethyl)phenyl]-2-propenoic acid (Compound 23) was prepared as outlined in Scheme IV. A mixture of o-bromobenzyl bromide (10.45 g; 41.81 mmol) and sodium cyanide (2.55 g; 52.25 mmol) in 100 ml of DMSO was heated at 60° C. for 5 hours. After being cooled, the reaction mixture was diluted with 200 ml of water and 200 ml of ethyl acetate. The layers were separated and the aqeous layer was extracted with any additional 100 ml of ethyl acetate. The combined organic layers were dried and concentrated, and the residue was purified on a flash column, eluting with 10% ether/hexane to obtain 6.63 g (81%) of 2-bromobenzyl cyanide 19, ¹H NMR (CDCl₃): δ3.83 (s, 2H); 7.18 (m,1 h); 7.29 (t, 1H); 7.52 (d, 1H); 7.60 (d, 1H).

A solution of lithium aluminum hydride (15 mmol) in THF (30 ml) was cooled to 0° C. and nitrile 19 was added as a THF solution (25 ml). After being stirred for 4 hours, the reaction mixture was quenched by the addition of 10 ml of water followed by 20 ml of 2N NaOH. The mixture was filtered through Celite to remove solids and the filter cake was washed with 2×100 ml of ethyl acetate. The layers were separated and the organic phase was washed with 2×50 ml of water, dried and concentrated to obtain 600 mg (55%) of oily product 2-bromophenethylamine 20, ¹H NMR (CDCl₃): δ2.79 (t, 2H); 2.85 (t, 2H); 7.21 (m, 4H).

A solution of amine 20 (500 mg; 2.5 mmol) and di-tert-butyl carbonate (630 mg; 2.87 mmol) in CH₂Cl₂ (15 ml) was stirred overnight. It was diluted with 100 ml of CH₂Cl₂ and washed with saturated aqueous sodium bicarbonate solution (2x) and brine (3x) and dried and concentrated. The residue was chromatographed eluting with 10% hexane/ethyl acetate to obtain 720 mg (96%) of thick oil N-(tert-butyloxycarbonyl)-2-bromophenethylamine 21, ¹H NMR (CDCl₃): δ1.42 (s, 9H); 2.89 (t, 2H); 3.91 (m, 2H); 4.55 (br, 1 H); 7.00 (m 1H); 7.15 (m, 1H); 7.20 (m, 1H); 7.43 (d, 1H).

Methyl acrylate (244 mg; 2.84 mmol) was added to a solution of bromide 21 (720 mg; 2.36 mmol) in DMF (3 ml) in a sealable tube. Triethylamine (710 mg; 7 mmol) was added next, followed by PdCl₂(Ph₃P)₂(35 mg; 0.05 mmol). The tube was charged with argon, sealed and heated to 90° C. for 24 hours. After being cooled, the tube's contents were diluted with 10 ml of ethyl acetate and 30 ml of water. The product was extracted into 3×50 mL ethyl acetate; the organic layers were concentrated and chromatographed (30% ethyl acetate/hexane) to provide 340 mg of the acrylate 22 ¹H NMR (CDCl₃): δ1.49 (s, 9H); 2.93 (t, 2H); 3.35 (m, 2H); 3.83 (s, 3H); 4.55 (br, 1H); 6.38 (d, 1H); 7.20 (m, 3H); 7.45 (d, 1H); 7.95 (d, 1H).

A mixture of acrylate 22 (320 mg; 1.05 mmol) and lithium hydroxide monohydrate (70 mg; 1.5 mmol) in 15 ml of THF and 3 ml of water was stirred for 24 hours at room temperature. The pH was adjusted to 3 by the addition of 10% aqueous citric acid and the product was extracted into ethyl acetate. Drying and removal of the solvent in vacuo furnished 280 mg of N-Boc-protected 3-[2-(aminoethyl)phenyl]-2-propenoic acid (Compound 23) as a white solid, ¹H NMR (CDCl₃): δ1.43 (s, 9H); 2.98 (m, 2H); 3.34 (m, 2H); 6.40 (d, 1H, J =16); 7.28 (m, 2H); 7.34 (t, 1H); 7.61 (d, 1H); 8.09 (d, 1 H). IR (CDCl3): 3157, 2983, 1795, 1697, 1635, 1471, 1381, 910, 730 cm⁻¹.

EXAMPLE 7

Synthesis of N-Boc-protected 4-amino-2-butenoic acid

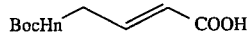   27

N-Boc-protected 4-amino-2-butenoic acid (Compound 27) was prepared as illustrated in Scheme V. To a cooled solution of N-(tert-butyloxycarbonyl)glycine (5.0 g; 28.5 mmol), N,O-dimethylhydroxyl- amine hydrochloride (3.06 g; 31.4 mmol), 4-dimethylaminopyridine (350 mg; 2.85 mmol) and 1-(3-dimethylaminopropyl)-3-ethylcarbodiimide (6.27 g; 32.8 mmol) in 100 ml of CH₂Cl₂ was added triethylamine (4.1 ml; 29.1 mmol). The mixture was stirred overnight and then washed successively with 10% aqueous citric acid (2x), saturated aqueous sodium bicarbonate solution (2x) and brine (2x). The solvent was evaporated to provide 4.55 g (73%) of the methoxamide 24 as a snow-white powder, ¹H NMR (CDCl₃): δ1.55 (s, 9H); 3.21 (s, 3H); 3.73 (s, 3H); 4.08 (m, 2 H); 5.22 (br, 1H).

Lithium aluminum hydride (1.72 ml of a 1.0M solution in THF: 1.72 mmol) was added to a cooled (0° C.) solution of methoxamide 24 (300 mg; 1.38 mmol) in THF (15 ml). The mixture was stirred for 20 minutes and then hydrolyzed with 7 ml of 5% aqueous KHSO₄ solution. Ether (35 mL) was added and the layers were separated. The aqueous layer was extracted with an additonal 3×35 ml of ether, and the combined organic phases were washed with 3N HCl, saturated sodium bicarbonate, and brine, and dried and concentrated to provide 130 mg (59%) of the aldehyde 25 as an oil, ¹H NMR (CDCl₃): δ1.48 (s, 9H); 4.15 (m, 2 H); 5.20 (br, 1H); 9.63 (s, 1H).

A solution of aldehyde 25 (5.5 g; 34.5 mmol) and methyl triphenylphosphoranylidene acetate (12.7 g; 38.01 mmol) in acetonitrile (100 ml) was refluxed overnight. The acetonitrile was removed under reduced pressure, ether was added to the residue, and the material was filtered to remove solids; the filter cake was washed with additional ether. The filtrate was concentrated and purified by flash chromatography, eluting with 20% ethyl acetate in hexane to obtain 3.0 g (40%) of ester 26; proton NMR indicated that the product had exclusively trans double bond geometry. ¹H NMR (CDCl₃): δ1.50 (s, 9H); 3.72 (s, 3H); 3.90 (m, 2 H); 4.68 (br, 1H); 5.91 (d, 1H); 6.88 (d, 1H).

To a stirred solution of the ester 26 (3.0 g; 13.94 mmol) in THF (60 mL) at 0° C. was added a solution of 0.88 g lithium hydroxide monohydrate in 21 ml of water in a dropwise fashion. The mixture was stirred for 1 hour at 0° C. and 12 hours at room temperature. The THF was removed under reduced pressure and the residue was washed with ether (2x). The aqueous layer was diluted with water and the pH was adjusted to the Congo Red indicator end point and extracted with ethyl acetate (2x). The combined extracts were dried and concentrated to provide 2.6 g (95%) of N-Boc-protected 4-amino-2-butenoic acid (Compound 27) as a white solid, ¹H NMR (D₂O): δ1.22 (s, 9H); 3.60 (d, 2H); 5.65 (d, 1 H); 6.33 (d, 1

EXAMPLE 8

Synthesis of N-Boc-protected 6-amino-4,5-(1,2-cyclohexyl)-2-hexenoic acid

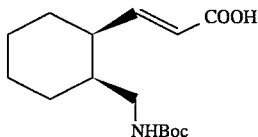   31

N-Boc-protected 6-amino-4,5-(1,2-cyclohexyl)-2-hexenoic acid (Compound :31) was prepared as outlined in Scheme VI. A solution of (−)-(1R, 6S)-cis-8-oxabicyclo [4.3.0]nonan-7-one (Jakovac, I. J.; Goodbrand, H. B.; Lok, K. P.; Jones, J. B. J. Am. Chem. Soc. 1982, 104, 4659) (1.74 g; 12.41 mmol) in toluene (30 ml) was cooled to −78° C. and treated with diisobutylaluminum hydride (10 ml of a 1.5M solution in toluene, 15 mmol). This mixture was stirred for 45 minutes. In a separate flask, a suspension of sodium hydride (1.14 g of a 60% dispersion in oil; 28.6 mmol) in THF (25 ml) was cooled to −78° C. and a solution of methyl diethylphosphonoacetate (5.47 g; 26 mmol) in THF (15 ml) was added dropwise. After being stirred for 45 minutes, the lactol reduction mixture was added via canula to this phosphonate anion solution, and the resulting mixture was stirred overnight while coming to room temperature. It was quenched with a saturated aqueous ammonium chloride solution and extracted into ethyl acetate. The organic phase was washed with water and brine, dried, and concentrated. The product was purified on a flash column, eluting with 20% ethyl acetate/hexane, to obtain 1.38 g of hydroxyacrylic ester 28, ¹H NMR (CDCl₃): δ1.28–1.88 (m, 9H); 2.67 (m, 1H); 3.41 (d, 2H); 3.71 (s, 3H); 5.85 (d, 1H); 7.11 (m, 1H).

Pyridinium chlorochromate (3.23 g; 15 mmol) added to a solution of alcohol 28 (1.0 g; 5.0 mmol) in 30 ml of methylene chloride, and the resulting solution was stirred for 24 hours at room temperature. The reaction mixture was diluted with 100 ml of ethyl acetate, filtered through Celite, and washed with 3×50 ml of water. The organic phase was dried and freed of solvent, and the residue was purified on a flash column, eluting with 10% ethyl acetate in hexane, to obtain 280 mg of aldehyde 29, $^1$H NMR (CDCl$_3$): δ1.28 (m, 4H); 1.81 (m, 3H); 1.92 (m, 1H); 2.22 (m, 1H); 2.43 (m, 1H); 3.78 (s, 3H); 5.83 (d, 1 H); 6.83 (m, 1H).

A mixture of aldehyde 29 (275 mg; 1.40 mmol), ammonium acetate (1.08 g; 14 mmol) and sodium cyanoborohydride (65 mg; 0.98 mmol) in 10 ml of methanol was stirred at room temperature for 48 hours. The mixture was quenched with 10% aqueous citric acid solution and stirred for several minutes, then made strongly basic (pH 10) with 1N NaOH and extracted with ethyl acetate (2×50 mL). The organic phases were washed with brine, dried and concentrated to obtain 250 mg of an oil. This was taken up in 10 ml of methylene chloride, treated with di-tert butyl dicarbonate (630 mg; 2.87 mmol) and stirred at room temperature overnight. The mixture was concentrated to dryness and flash chromatographed on a silica column, eluting with 10% ethyl acetate in hexane, to obtain 250 mg of 30, $^1$H NMR (CDCl$_3$): d 1.24 (s, 9H); 1.28–1.90 (m, 9H); 2.61 (m, 1H); 3.34 (m, 2H); 3.75 (s, 3H); 6.95 (m, 1H).

A solution of ester 30 (240 mg) and lithium hydroxide monohydrate (100 mg) in 10 ml of 2:1 methanol: water was stirred for 24 hours at room temperature and then made acidic (pH 3) with 10% aqueous citric acid solution. The product was extracted into ethyl acetate, and the solvent was removed in vacuo to provide 200 mg of N-Boc-protected 6-amino-4,5-(1,2-cyclohexyl)-2-hexenoic acid (Compound 31), $^1$H NMR (CDCl3): δ1.27 (s, 9H); 1.25–1.88 (m, 9H); 2.58 (m, 1H); 3.38 (m, 2H); 5.79 (d, 1 H); 6.83 (m, 1H).

Repetition of the above synthesis, starting with the enantiomeric lactone provided the enantiomeric acid 32.

EXAMPLE 9

Preparation of 3-[3-(tert-Butoxycarbonylaminomethyl)phenyl]-2-propenoic Acid

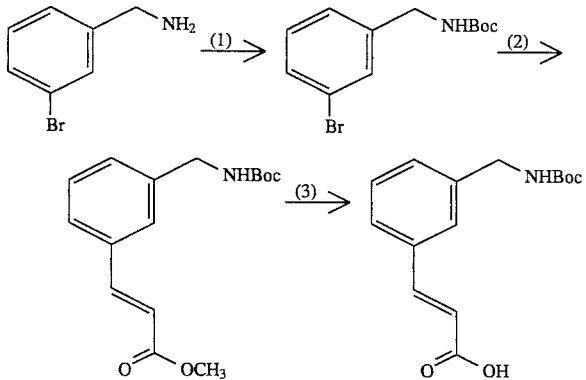

(1) Preparation of 1-(tert-butoxycarbonylamino methyl)-3-bromobenzine.

Sodium carbonate (7.95 g, 75 mmol) was added to a stirred solution of 11.1 g (50 mmol) of 3-bromobenzylamine hydrochloride in 75 ml of water. The resulting mixture was stirred at 0° C. for 5 minutes and then 12.0 g (55 mmol) of di-tert-butyl dicarbonate in 25 ml of 2-propanol was added dropwise. After being stirred at ambient temperature for 3 hours the mixture was diluted with a mixture of 100 ml of water and 100 ml of ether. The aqueous phase was extracted with ether. The combined ether extracts were washed successively with 1N hydrochloric acid, water and brine, dried (Na$_2$SO$_4$) and concentrated to provide the product (14.2 g, 99%) as crystals, mp 55°–59° C.

(2) Preparation of methyl 3-[(3-tert-butoxycarbonylaminomethyl)phenyl]-2-propenoate.

A mixture of 6.0 g (21 mmol) of 1-(tert-butoxycarbonylaminomethyl)-3-bromobenzine, 9.0 ml (64 mmol) of triethylamine, 2.7 ml of methyl acrylate and 0.5 g (0.7 1 mmol) of (triphenylphosphine) palladium (II) chloride was sealed in a heavy-walled Pyrex Teflon screw-capped flask and heated at 110°–120° C. for 48 hours. After being cooled to 25° C. the reaction mixture was suspended between 50 ml of ethyl acetate and 150 ml of water. The aqueous phase was extracted with ethyl acetate. The combined organic phases were washed with water and brine, dried (Na$_2$SO$_4$) and concentrated. The residue was chromatographed on a silica gel column that was eluted with a 2 to 25% gradient of ethyl acetate in hexane to afford 4.16 g (68%) of the product as an oil.

(3) Preparation of 3-[3-(tert-butoxycarbonylaminomethyl)phenyl]-2-propenoic acid.

After a stirred mixture of 4.06 g (14 mmol) of methyl 3-[3-(tert-butoxycarbonyl aminomethyl)phenyl]-2-propenoate, 3.0 g (28.3 mmol) of sodium carbonate, 75 ml of water and 75 ml of methanol was heated at reflux for 5 hours, the produced methanol was distilled off and the solution was cooled to 0° C. and acidified with 1N hydrochloric acid. The resulting mixture was extrated with ethyl acetate. The extracts were washed with brine, dried (Na$_2$SO$_4$) and concentrated. Recrystallization of the residual solid from 1:3 ethyl acetate-hexane gave 3.52 g (91%) of the product as crystals, mp 121°–123° C.

EXAMPLE 10

Preparation of 3-{2-[3-(tert-Butoxycarbonylamino)propyl]phenyl}-2-propenoic Acid.

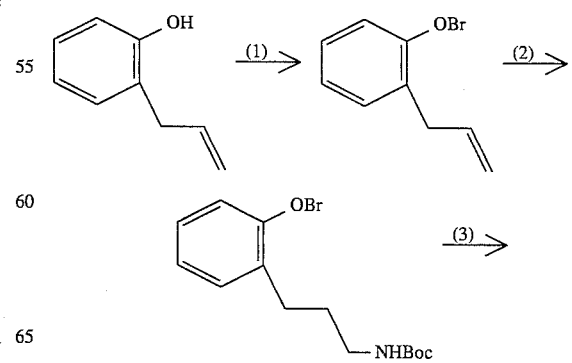

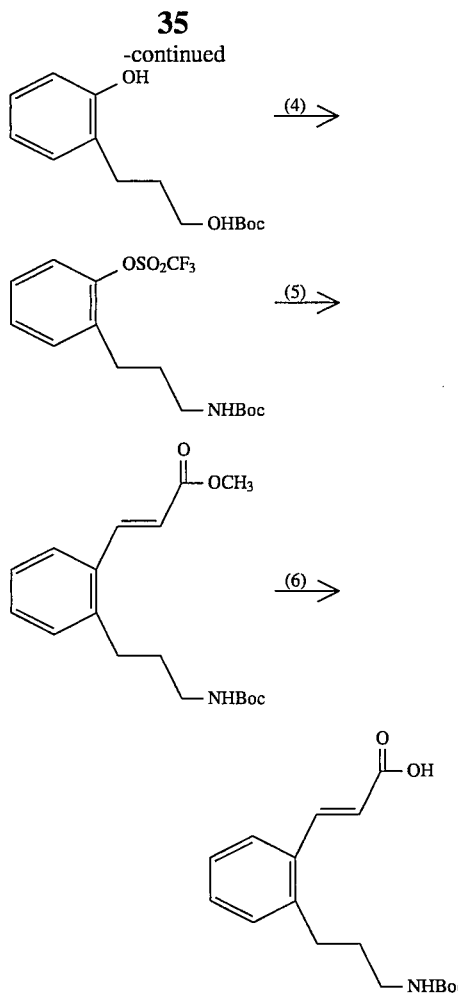

(1) Preparation of 2-allylphenyl benzyl ether.

A solution of 6.71 (50 mmol) of 2-allylphenol in 50 ml of dimethylformamide was added dropwise to a stirred suspension of 2.20 g (55 mol) of a 60% dispersion of sodium hydride in mineral oil in 30 ml of dimethylformamide. The mixture was stirred at 25° C. for 1 hour and then a solution of 5.95 ml (50 mmol) of benzyl bromide in 20 ml of dimethylformamide was added dropwise. After the resulting mixture was stirred at 25° C. for 18 hours 500 ml of water was added and the mixture was extracted with ether. The ether extracts were washed with water and brine, dried ($Na_2SO_4$) and concentrated. Chromatography of the residue on a silica gel column, eluting with a 0 to 10% gradient of ethyl acetate in hexane afforded 9.68 g (86.4%) of the product as a colorless liquid.

(2) Preparation of
N-(tert-butoxycarbonyl)-3-[2-(benzyloxy)phenyl]
propylamine.

A 1M solution of borane in tetrahydrofuran (10 ml, 10 mmol) was added dropwise to a stirred solution of 6.5 g (29.2 mmol) of 2-allylphenylbenzyl ether in 50 ml of tetrahydrofuran at 0° C. The resulting solution was stirred as 2.31 g (20 mmol) of hydroxylamine-O-sulfinic acid was added in portions. After the resulting mixture was stirred and refluxed for 3 hours, it was cooled to 25° C. and 25 ml of 6N hydrochloric acid in 100 ml of water was added. Following extraction with ether, the aqueous solution was made basic with 5N sodium hydroxide. The mixture was extracted with ether. The ether extracts were washed with brine, dried ($Na_2SO_4$) and filtered. Di-tert-butyl dicarbonate (6.5 g, 30 mmol) was added to the filtrate. The resulting mixture was stirred at ambient temperature for 18 hours. The ether solution was washed with brine, dried ($Na_2SO_4$) and concentrated. Silica gel column chromotagraphy of the residue eluting with 10% ethyl acetate in hexane gave 4.64 g (48.3%) of the product as a colorless oil that crystallized on standing, mp 50°–52° C.

(3) Preparation of
2-[3-(tert-butoxycarbonylamino)propyl]phenol.

A mixture of 4.64 g (14.1 mmol) of N-(tert-butoxycarbonyl)-3-[2-(benzyloxy)phenyl]propylamine, 1.0 g. of 5% palladium-on-carbon catalyst and 95 ml of ethanol was hydrogenated by shaking in a Parr apparatus using an initial pressure of 40 psi of hydrogen for 24 hours until hydrogen uptake was completed. The mixture was filtered and the filtrate was concentrated. The residue was chromatographed on a silica gel column which was eluted with a 5 to 20% gradient of ethyl acetate in hexane to give 3.14 g (88.7%) of the product as colorless crystals, mp 75°–77° C.

(4) Preparation of
2-[3-tert-butoxycarbonylamino)propyl]phenyl
trifluromethane-sulfonate.

Trifluoromethanesulfonic anhydride (2.27 ml, 13.5 mmol) was added dropwise to a stirred solution of 3.04 g (12.1 mmol) of 2-[3-(tert-butylcarbonylamino)propyl]phenol in 10 ml of pyridine at 0° C. After the reaction mixture was stirred at ambient temperature for 18 hours, 100 ml of water and 100 ml of ether were added. The layers were separated and the aqueous phase was extracted with ether. The extracts and ether phase were combined, washed successively with 1N hydrochloric acid, water and brine, dried ($Na_2SO_4$) and concentrated. The residue was chromatographed on a silica gel column which was eluted with a 1 to 25% gradient of ethyl acetate in hexane to afford 3.3 g (71%) of the product as a colorless oil.

(5) Preparation of methyl
3-{2-[(tert-butoxycarbonylamino)propyl]phenyl}-
2-propenoate.

A solution of 3.27 g (8.54 mmol) of 2-[3-(tert-butoxycarbonylamino)propyl]phenyl trifluoromethanesulfonate, 3.62 ml (26 mmol) of triethylamine 1.15 ml (12.8 mmol) of ethyl acrylate and 0.2 g (0.3 mmol) of his (triphenylphosphine) palladium (II) chloride was heated at 110° C. in a sealed heavy-walled Pyrex, Teflon screw-capped flask for 16 hours. Ethyl acetate (100 ml) and water (100 ml) were added to the reaction mixture after it was cooled to 25° C. The aqueous phase was extracted with ethyl acetate. The combined organic extracts were washed with water and brine, dried ($Na_2SO_4$) and concentrated. The residue was chromotographed on a silica gel column, eluting with a 5 to 25% gradient of ethyl acetate in hexane to afford 1.85 g (68%) of the product as an oil.

(6) Preparation of 3-{2-[3-(tert-butoxycarbonyl
amino)propyl)phenyl}-2-propenoic acid.

A stirred mixture of 1.81 g (5.7 mmol) of methyl 3-{2-[3 -(tertbutoxycarbonylamino)propyl]-phenyl}-2-propenoic, 1.59 g (15 mmol) of sodium carbonate, 25 ml of water and 25 ml of methanol was heated under refluxed for 1.5 hours. After the produced methanol was distilled off, the solution was cooled to 0° C. and carefully acidified with 1N hydrochloric acid. The resulting mixture was extracted with ethyl acetate. The extracts were washed with brine, dried, ($Na_2SO_4$) and concentrated. Recrystallization of the residue from 1:3 ethyl acetate: hexane gave the product as 1.6 g (92.5%) colorless crystals, mp 122°–126° C.

EXAMPLE 11

Preparation of 5-[2-(tert-Butoxycarbonylaminomethyl)phenyl)]-2,4-pentadienoic Acid

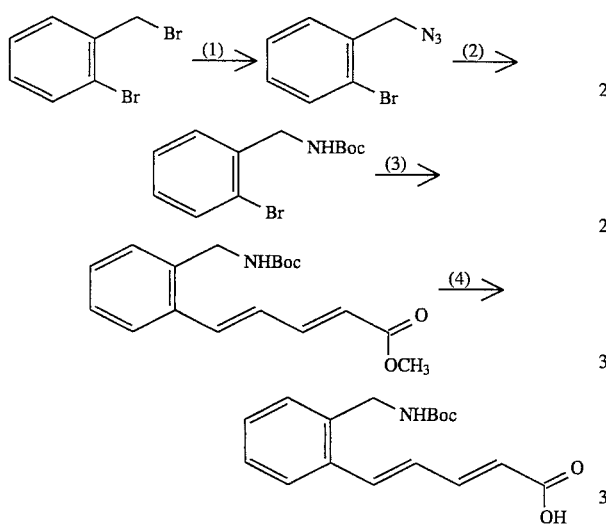

(1) Preparation of 1-azidomethyl-2-bromobenzene.

After a mixture of 30 g (120 mmol) of 1-bromomethyl-2-bromobenzene and 15.6 g (240 mmol) of sodium azide in 300 ml of dimethylformamide was stirred at 25° C. for 20 hours it was poured into 500 ml of water and extracted with ethyl acetate. The extracts were washed with water and brine, dried ($Na_2SO_4$) and concentrated to give 24.9 g (98%) of the product as an oil.

(2) Preparation of 1-(tert-butoxycarbonylaminomethyl)-2-bromobenzine.

Triphenylphospine (37.0 g, 14 1 mmol) was added in portions to a stirred solution of 24.9 g, 118 mmol) of 1-azidomethyl-2-bromobenzene in 300 ml of tetrahydrofuran and 30 ml of water. After the mixture was stirred at ambient temperature for 18 hours, 33.3 g (152.5 mmol) of di-tert-butyl dicarbonate was added. The mixture was stirred at 25° C. for 1 hour, at reflux for 1 hour, and then at 25° C. for an additional 2 hours. The reaction mixture was then concentrated. The residue was suspended in 200 ml of ether and 200 ml of water. The aqueous phase was extracted with ether. The combined ether extracts were washed with brine, dried ($Na_2SO_4$) and concentrated. Chromatography of the residue on a silica gel column, eluting with a 1 to 10% gradient of ethyl acetate in hexane gave 29.6 g (88%) of the product as colorless crystals, mp 50°–53° C.

(3) Preparation of methyl 5-[2-(tert-butoxycarbonylaminomethyl)phenyl]-2,4-pentadienoate.

A mixture of 3.0 g (10.5 mmol) of 1-(tert-butoxycarbonylaminomethyl)-2-bromobenzene, 4.5 ml (32.3 mmol) of triethylamine, 1.82 ml (15.7 mmol) of methyl 2,4-pentadienoate and 0.2 g (0.28 mmol) of bis (triphenylphosphine) palladium (II) chloride was sealed in a heavy-walled Pyrex, Teflon screw-capped flask and heated at 100° C. for 40 hours. After being cooled to 25° C. the reaction mixture was diluted with 150 ml of water and 50 ml of ether. The aqueous phase was extracted with ether. The combined ether extracts were washed with water and brine, dried ($Na_2SO_4$) and concentrated. The residue was chromatographed on a silica gel column that was eluted with a 5 to 10% gradient of ethyl acetate in hexane to give 1.6 g (53.3%) of colorless needles, mp 96°–97.5° C. after recrystallization from 1:3 ether:hexane.

(4) Preparation of 5-[2-(tert-butoxycarbonylaminomethyl)phenyl]-2,4-pentadienoic acid.

A stirred mixture of 0.85 g (2.7 mmol) of methyl 5-[2-(tertbutoxycarbonylaminomethyl)phenyl]-2,4 -pentadienoate, 1.17 g (11 mmol) of sodium carbinate, 15 ml of water and 15 ml of methanol was heated at reflux for 2 hours. After the produced methanol was distilled off, the solution was cooled to 0° C. and carefully acidified with 1N hydrochloric acid. The resulting mixture was extracted with methylene chloride and the extracts were washed with brine, dried ($Na_2SO_4$) and concentrated. Recrystallization of the residue from 1:3 methylene chloride:hexane gave 0.7 g (86%) of the product as crystals, mp 179°–182° C. (dec).

EXAMPLE 12

Preparation of Pseudopeptide

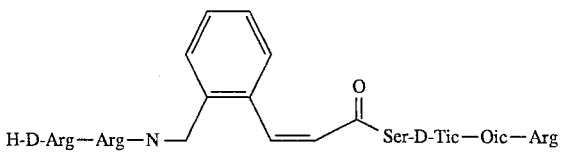

The indicated pseudopeptide was synthesized manually using standard solid phase methods and t-Boc chemistry.

1. Boc-Arg(Tos)-PAM resin was used for the purpose. Amino acids and the Boc-protected derivatives of olefinic aminoalkanoic acid prepared in Example 1 were introduced according to the sequence of the pseudopeptide.

2. Deprotection: The N-terminal t-Boc protection was accomplished by treating the resin-aa/resin-peptide with trifluoroacetic acid/methylene chloride (1:1) for two minutes followed by a similar treatment for 30 minutes.

3. The resin was then washed with methylene chloride and ethanol and neutralized with 10% triethylamine/methylene chloride or 10% diisopropylethylamine/methylene chloride.

4. Couplings: All couplings were carried out using the active ester of the amino acid. The active esters of the individual amino acids were generated prior to their introduction into solid phase synthesis. Five equivalents (with respect to loading of the first amino acid on the resin) of the amino acid, hydroxybenzotriazole hydrate and dicyclohexylcarbodiimide or diisopropylcarbodiimide, was incubated for 30 minutes at 0° C. in dimethylformamide or methylene chloride/dimethylformamide (1:1) for this purpose. Couplings were followed until no more free amine was detected on the resin using qualitative ninhydrin analysis (Kaiser test). Different unnatural amino acids behave differently during ninhydrin analysis and the color of the resin (after deprotection and coupling) depends on the specific amino acid being used.

5. After coupling, the resin-peptide was washed with dimethyl formamide and methylene chloride before commencement of another cycle of the synthesis.

6. The finished peptidyl-resin was cleaved from the resin using HF (10 mL/g of resin) in the presence of 10% anisole (scavenger). After removal of HF, the peptide resin was washed with ether and the peptide was extracted with 0.1% TFA or 0.2% acetic acid. Lyophilization yielded crude peptide, usually flaky yellow solids were obtained at this stage.

7. The crude peptide was purified using reverse phase high performance liquid chromatography on a $C_{18}$ column using a gradient of water/acetonitrile (both containing 0.1% trifluoroacetic acid or 0.2% acetic acid). The pure fractions were determined by analytical HPLC, on a Vydac $C_{18}$ column using a gradient of water/acetonitrile (both containing 0.1% trifluoroacetic acid) and pooled together and lyophilized to give flaky white solids.

8. Peptides were analyzed by analytical reverse phase HPLC on a Vydac $C_{18}$ column using a gradient of water/acetonitrile (both containing 0.1% trifluoroacetic acid), and fast atom bombardment mass spectroscopy.

EXAMPLE 13

Preparation of Additional Pseudopeptides

The following pseudopeptides were synthesized according to a precedure similar to that outlined in Example 12 using the Boc-protected aminoalkenoyl spacers synthesized in Examples 1 through 11.

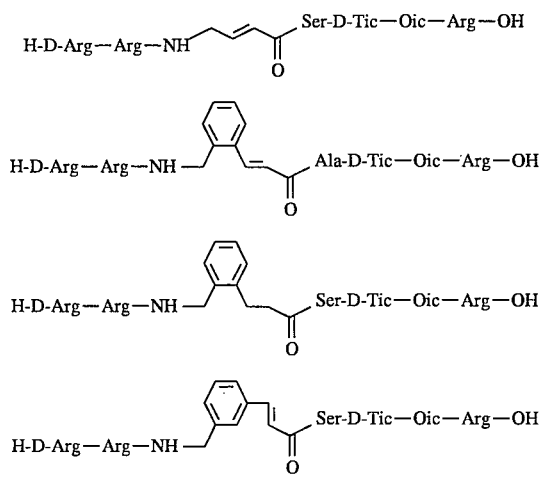

EXAMPLE 14

Preparation of $B_1$ Receptor Antagonists

The $B_1$ receptor antagonists corresponding to the pseudopeptides prepared in Example 12 and Example 13, wherein the C-terminal arginine is deleted, are prepared in an analogous manner. The solid phase synthesis is initiated using Boc-Oic-PAM resin obtainable from a commercial supplier (Advanced Chemtech, Louisville, Ky.).

EXAMPLE 15

Bradykinin Binding Procedures

Guinea Pig Ileum Binding

Binding of $^3$H-bradykinin was performed using the method of D. C. Manning, R. Vavrek, J. M. Stewart, and S. H. Snyder, *J. Pharmacol. Exp. Ther.*, (1986), 237, 504. The tissues used in the binding assay were terminal ileum from male Hartley guinea pigs (150–350 g). After dissection, tissues were placed in 20 volume of ice-cold buffer A (25 mM TES containing 0.2 g/l of 1,10-phenanthroline adjusted of pH 6.8 with ammonium hydroxide) and homogenized using a Polytron Tissumizer at setting 6 for 15 seconds. The homogenate was centrifuged at 50,000× g for 10 minutes, the supernatant discarded, and the pellet resuspended in ice-cold buffer A by homogenization with the Polytron. Each tissue was homogenized and centrifuged three times. The final pellet was resuspended in buffer A containing bovine serum albumin (1 g/l) and Bacitracin (0.14 g/l) to a final volume of 170 ml/g of the original tissue weight. The binding assay consisted of 1 mM in 12×75 mm polyproylene tubes: 50 μl $^3$H-bradykinin (20,000 dpm, ~0.3 nM in the final assay volume), 100 μl displacing drug in buffer A, and 750 μl tissue homogenate. Each tray contained tubes, to which no drug was added to measure maximum binding and tubes to which bradykinin (1 μM final concentration) had been added, to measure specific binding. Specific binding accounted for 96–98% total binding. Tubes were incubated for 90 minutes at ambient temperature. The assays were terminated by filtration over Whatman GF/B glass fiber filters that had been pretreated for 2 hours with polyethyleneimine (2 g/l) using a Brandel Tissue Harvester, followed by washing with 4×1 ml aliquots of ice-cold 50 mM Tris, pH 7.4. Filters were dissolved in Ready-Safe Fluor (Beckman)

for at least 90 minutes before quantitation by liquid scintillation spectrometry. Kd values were determined using saturation binding and analysis by EBDA (G. A. MacPherson, *J. Pharmacol. Methods*, (1985), 213), followed by LIGAND (P. J. Munson, D. Rodbard, *Anal. Biochem.*, (1980), 220). $K_i$ values were determined using competitive analysis followed by EBDA and LIGAND. The test results obtained are shown in Table I.

Human Bradykinin Receptor Binding

The human bradykinin $B_2$ receptor was cloned by Hess et al. (*Biochem. Biophys. Res. Comm.*, (1992), 184, 260–268) A human bradykinin $B_2$ receptor was expressed in CHO/K cells. Briefly, approximately $2\times10^6$ plaques from a human uterus λgt10 cDNA library (Clontech Laboratories; Palo Alto, Calif.) were screened using a PCR fragment containing the coding region of the rat $B_2$ receptor. This probe was generated by random-primed synthesis in the presence of $\alpha[^{32}P]dATP$. Duplicate filters were hybridized overnight at 42° C. in 1M NaCl, 50 mM Tris pH 7.5, 5X Denhardt's, 200 µg/ml salmon sperm DNA, 1% SDS, and 20% formamide. The filters were washed at 65° C. in 1X SSC and 1% SDS. Coincident positively hybridizing plaques were purified and rescreened with the same probe and stringency conditions. EcoRI fragments of positive clones were inserted into Bluescript/KS II+vector (Stratagene; La Jolla, Calif.) for sequence determination.

The nucleotide sequence of the cloned human $B_2$ receptors was determined using double-stranded DNA and the dideoxy chain termination method. Commercially available T3 and T7 oligonucleotides (USB; Cleveland, Ohio) and synthetic 21-mer oligonucleotides (DNA/RNA Synthesizer; Applied Biosystems Inc.; Palo Alto, Calif.) from both the known rat sequence and the determined human sequence were used to identify the nucleotide sequence from the 5' untranslated end to the Bgl II site in the 3' untranslated end of the clone. The HindIII/XbaI fragment of one full-length clone, 126A, was inserted into pcDNAI neo vector (Invitrogen; San Diego, Calif.) for expression in mammalian cell lines.

CHO/K cells were plated in 2 ml of growth medium (Ham's F12 with 10% FBS) per 6 well plate and incubated at 37° C., 5% $CO_2$ until they were 60% confluent. For each well, 4, 12, and 16 µg of DNA was diluted in 100 µl Opti-MEM I reduced serum medium (Gibco/BRL; Gaithersburg, Md.). 12 µl of TransfectASE reagent (Gibco/BRL) was diluted in a separate aliquot of 100 µl Opti-MEM I. The DNA and TransfecASE solutions were combined, mixed gently, and incubated at 25° C. for 15 minutes. This solution was then diluted to 1 ml with Opti-MEM I. Each well was washed twice with Opti-MEM I and 1 ml of the DNA/TransfectAse complex was added to each well. After a 5 hour incubation at 37° C. and 5% $CO_2$, 1 ml of Ham's F12 with 20% FBS was added to each well and cells were incubated overnight. Media was replaced with growth medium and incubated for additional 24 hours.

Cells were harvested by trypsinization and replated in selection medium (Ham's F12, 10% FBS and 500 µg/ml Geneticin (Gibco/BRL). Media was replaced every 48 hours for 2 weeks. Any colonies remaining after selection were transferred to separate 10 cm dishes, grown to confluency and positive clones were determined by binding of 3H-NPC 17731 a bradykinin antagonist peptide described by Burch et al., (DuPont Biotech update, 1992; 4:127–140) and having the structure D-Arg-Arg-Pro-Hyp-Gly-Phe-Ser-DHypeE-(transpropyl)-Oic-Arg. Colonies expressing the receptor were put out at limiting dilution. Cells were expanded and positive clones were identified as above. A cell line designated H2O.2 was used to quantitate binding of the compounds of the invention to the human bradykinin $B_2$ receptor.

Radioligand Binding Assays

H2O.2 cells were grown to confluency in Ham's F12 media containing 10% FBS and 500 µl/ml Geneticin. Growth media was aspirated and the monolayer washed once with Dulbecco's PBS without Ca++ and Mg++. Cells were scraped in Dulbecco's PBS and centrifuged at 2000x g for 10 minutes. Pellets were resuspended in 25 mM TES, 1 mM 1,10-phenanthroline pH 6.8 buffer and homogenized using a Ploytron at setting 5 for 10 seconds. An aliquot was taken for a protein determination using a BioRad protein assay kit. Membranes were centrifuged at 48000x g for 10 minutes at 4° C. Pellets were resuspended in the TES buffer with 0.1% BSA and 0.014% bacitracin. 0.5 ml aliquots were frozen in liquid $N_2$ and stored at −80° C. for up to 2 weeks.

Membranes from H2O.2 cells previously prepared were thawed at 37° C. and diluted in 25 mM TES, 1 µM 1,10-phenanthroline pH 6.8 containing BSA and bactiracin. For saturation binding assays, increasing concentrations of 3H-bradykinin or $^3H$-NPC 17731 were incubated with 16.5 µg of membrane protein in a total volume of 3 ml of the same buffer. Non-specific binding was determined with 1 µM bradykinin. The tubes were incubated 90 minutes at 25° C. and the assay was terminated by rapid vacuum filtration onto Whatman GF/B filters presoaked with 0.2% PEI for 3 hours followed by 2×3 ml aliquots of ice-cold 50 mM Tris, pH 7.4. Radioactivity was counted with a Beckman scintillation counter. The test results obtained are shown in Table I.

EXAMPLE 16

Determination of Bradykinin Antagonist Activity

The protocol was designed to identify compounds that possess antagonist activity at bradykinin receptors on intestinal (ileal longitudinal) smooth muscle.

Guinea pig intestine was removed and placed in a Petri dish containing Tyrodes solution and cut into 3–4 cm segments. The longitudinal muscle was separated from the underlying circular muscle using a cotton applicator (Paton and Zar, *J. Physiol.*, (1968), 194:13). Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 ml tissue baths to increase the concentration of bradykinin in the bath step-by-step without washing out after each single dose. Higher concentrations were added only after the preceding contraction had reached a steady value. When the next concentration step does not cause a further increase in contraction, it was assumed that the maximum effect had been obtained and the tissue was washed to remove bradykinin and allowed to recover for 15 minutes. Antagonism of badykinin responses in the presence of antagonist were determined by repeating the cumulative addition procedure for bradykinin after the tissue has been exposed to the antagonist for 5 minutes. Three or four different concentrations of antagonist are studied sequentially in the same preparations. Responses were expressed as a percentage of the maximum contraction elicited by bradykinin in the absence of antagonist. pA2 values were calculated by Schild analysis. The results obtained are shown in Table I.

The invention being thus described, it will be obvious that the same may be varied in many ways. Such variations are not to be regarded as a departure from the spirit and scope of the invention and all such modifications are intended to be included within the scope of the following claims.

EXAMPLE 17

Determination of $B_1$ Receptor Antagonist Activity

The ability of a pseudopeptide of the invention to antagonize $B_1$ receptor mediated inflammatory responses in vivo can be confirmed by testing the ability of the pseudopeptide to inhibit des $Arg^9$-bradykinin induced hypotension in rabbits that have been pretreated with lipopolysaccharide. It is known that, in the presence of inflammation-inducing substances, including polysaccharide and interleukin 1, $B_1$ receptors are upregulated and respond to des $Arg^9$-bradykinin to produce inflammatory responses, including hypotension.

Male New Zealand white rabbits (1.5–2.0 kg) are pretreated with a freshly made solution of LPS (10 µg/100 µl) 5 hr prior to anesthetizing with sodium phenobarbital i.v. The left carotid artery is cannulated for recording mean arterial blood pressure and the left jugular vein for des $Arg^9$-bradykinin (1 µg/kg) and the pseudopeptide to be tested. Animals are pulsed with a bolus of des $Arg^9$-bradykinin (3x) at 5 min intervals to produce a basal hypotensive response. Test pseudopeptide is then administered as a bolus prior to des $Arg^9$-bradykinin and its ability to antagonize the $B_1$-mediated hypotensive response is determined as % inhibition.

TABLE I

| Compound | 3HBK | Human $K_i$(nM) 3H17731 | Guinea Pig | pA$_2$(GPI) |
|---|---|---|---|---|
| H—D—Arg—Arg—NH—CH=CH—CH$_2$—C(O)—Ser—D—Tic—Oic—Arg—OH | | 229 | | |
| H—D—Arg—Arg—NH—CH$_2$—(o-phenyl)—CH=CH—C(O)—Ser—D—Tic—Oic—Arg—OH | 27 | | '120 ± 8 | |
| H—D—Arg—Arg—NH—CH$_2$—(o-phenyl)—CH=CH—C(O)—Ala—D—Tic—Oic—Arg—OH | | 278 ± 56 | | |
| H—D—Arg—Arg—NH—CH$_2$—(o-phenyl)—CH$_2$—CH$_2$—C(O)—Ser—D—Tic—Oic—Arg—OH | | 563 ± 146 | | |
| H—D—Arg—Arg—NH—CH$_2$—(m-phenyl)—CH=CH—C(O)—Ser—D—Tic—Oic—Arg—OH | | 496 ± 92 | | |
| H—D—Arg—Arg—NH—CH$_2$—(m-phenyl)—CH$_2$—CH$_2$—C(O)—Ser—D—Tic—Oic—Arg—OH | | 466 ± 73 | | |

TABLE I-continued

| Compound | 3HBK | Human K_1(nM) 3H17731 | Guinea Pig | pA_2(GPI) |
|---|---|---|---|---|
| 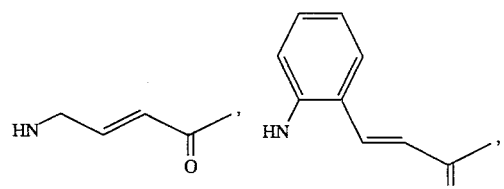 | 51 | 17 | | 6.10 |
| 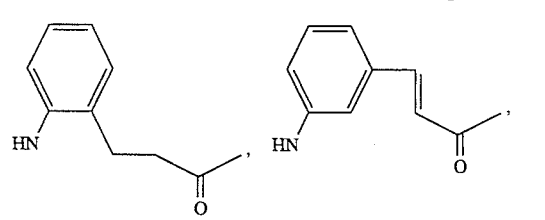 | | 23 | | |
| 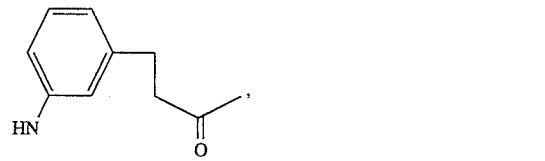 | | | | |

I claim:

1. A pseudopeptide which has an affinity for the bradykinin $B_1$ receptor having the formula $$A\text{-}B\text{-}C\text{-}D\text{-}E\text{-}F\text{-}C_n$$

wherein

A is selected from the group consisting of the L- and D-isomers of Arg and Lys;

B is selected from the group consisting of the L- and D-isomers of Arg and Lys;

C is selected from the group consisting of:

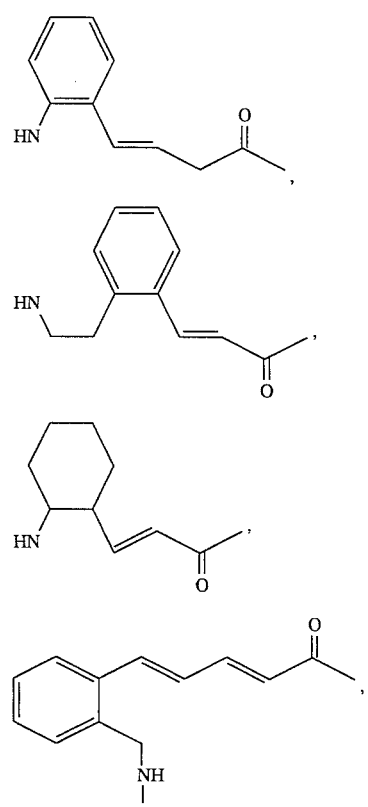

47
-continued

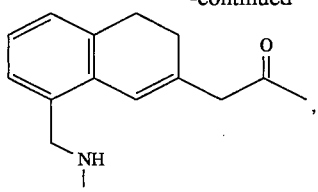

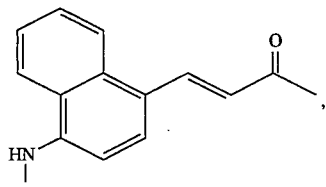

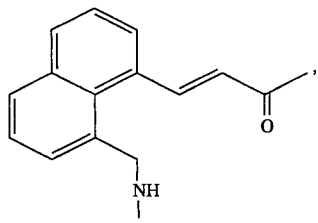

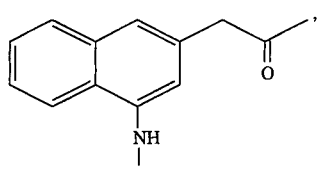

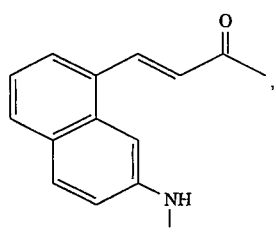

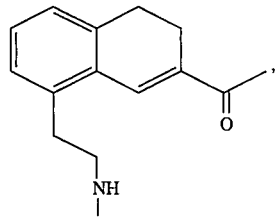

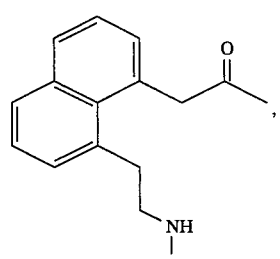

48
-continued

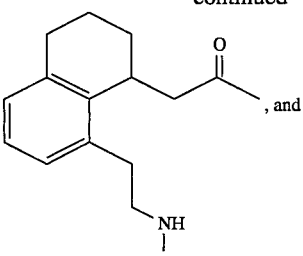, and

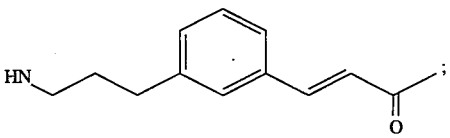;

D is a direct bond or selected from the group consisting of Ser, Thr, Gly and Val;

E is selected from the group consisting of a D-Phe, D-Tic and a D-trans-Hype;

F is selected from the group consisting of Oic, Aoc, Phe, Tic, and a Hype; and $C_n$ is selected from the group consisting of a hydroxyl moiety, an amino moiety and an alkoxy moiety; and pharmaceutically acceptable salts thereof.

2. A pseudopeptide of claim 1 wherein:

A is D-Arg;

B is Arg;

C is selected from the group consisting of:

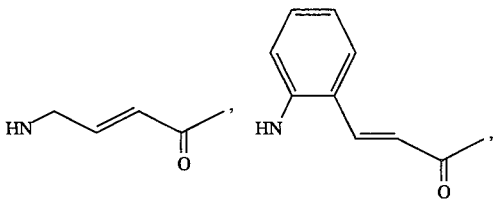

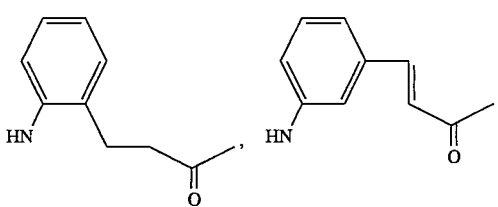

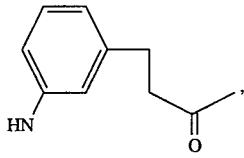

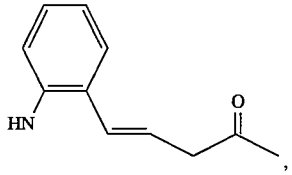

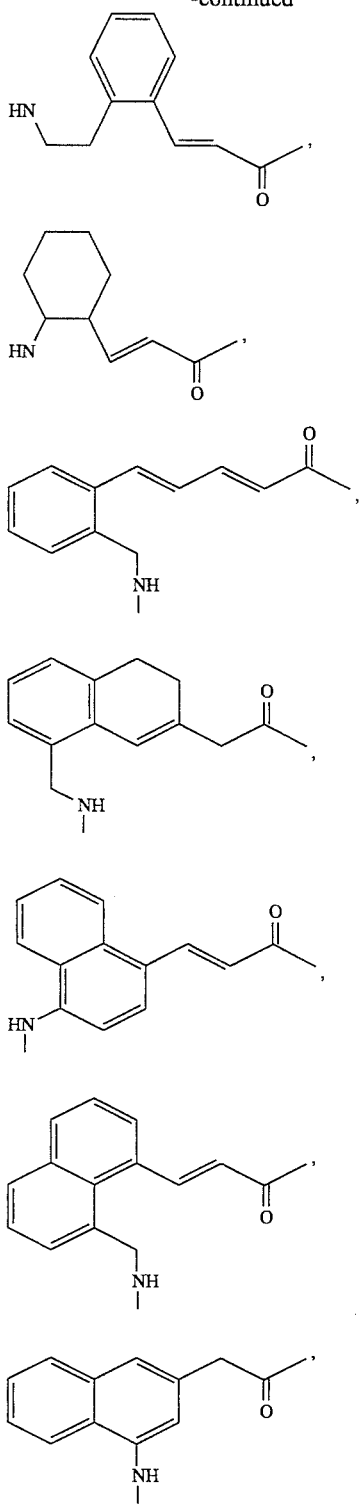
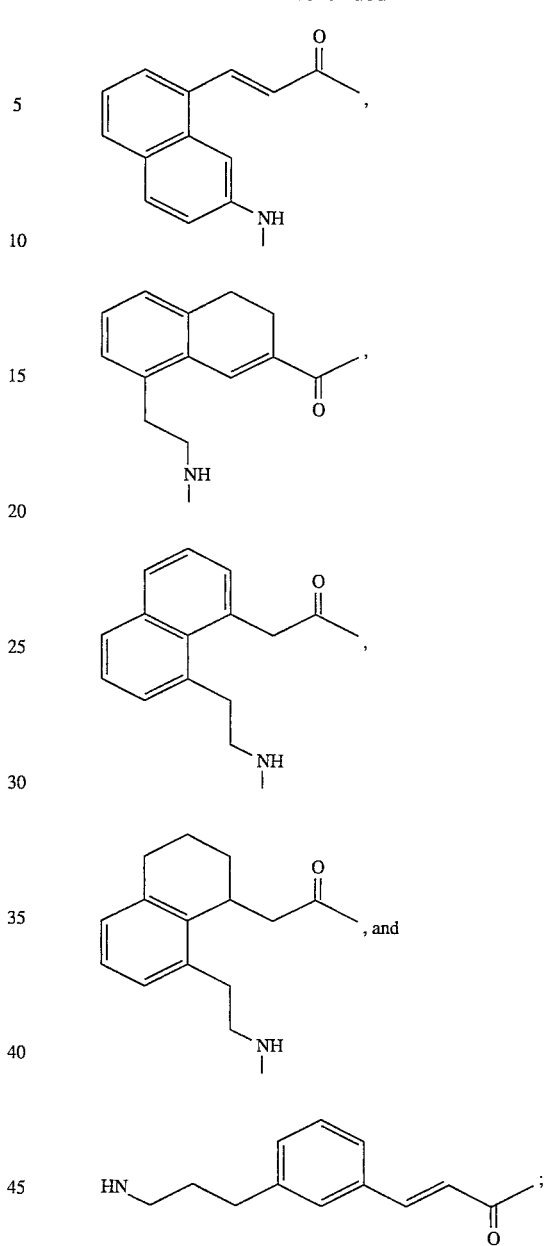
D is a direct bond or Ser:
E is selected from the group consisting of D-Phe, D-Tic, D-Hype(transpropyl), D-Hype(trans-thiophenyl), D-Hype(trans-phenylpropyl), D-Hype(trans-2-methylbutyl), D-Hype(trans-ethyl) and D-Hype(trans-methyl);
F is Oic; and
$C_n$ is OH.
* * * * *